(12) United States Patent
Thakur et al.

(10) Patent No.: US 9,872,448 B2
(45) Date of Patent: Jan. 23, 2018

(54) BIOREACTOR VESSEL FOR LARGE SCALE GROWING OF PLANTS UNDER ASEPTIC CONDITION

(71) Applicant: Council of Scientific & Industrial Research, New Delhi (IN)

(72) Inventors: Rajesh Thakur, Himachal Pradesh (IN); Anil Sood, Himachal Pradesh (IN); Paramvir Singh Ahuja, Himachal Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 194 days.

(21) Appl. No.: 14/415,711

(22) PCT Filed: Aug. 1, 2013

(86) PCT No.: PCT/IN2013/000478
§ 371 (c)(1),
(2) Date: Jan. 19, 2015

(87) PCT Pub. No.: WO2014/024211
PCT Pub. Date: Feb. 13, 2014

(65) Prior Publication Data
US 2015/0150203 A1    Jun. 4, 2015

(30) Foreign Application Priority Data

Aug. 6, 2012    (IN) .......................... 2445/DEL/2012

(51) Int. Cl.
*C12M 1/00*        (2006.01)
*A01G 31/02*    (2006.01)
(Continued)

(52) U.S. Cl.
CPC ............... *A01G 31/02* (2013.01); *A01G 9/16* (2013.01); *C12M 35/00* (2013.01)

(58) Field of Classification Search
CPC .... F16M 11/04; F16M 11/24; F16M 2200/02; F16M 2200/063; A01G 31/02; A01G 9/16
(Continued)

(56) References Cited

U.S. PATENT DOCUMENTS 2,536,292 A * 1/1951 Kollsman ............. F16L 27/082
                                                                277/399
2,554,048 A * 5/1951 Morrison .............. B65F 1/1442
                                                                220/324

(Continued)

FOREIGN PATENT DOCUMENTS

FR          2971117 A1 * 8/2012 ............. A01G 9/022
WO     WO 02/094416 A1    11/2002
(Continued)

*Primary Examiner* — Marc R Burgess
*Assistant Examiner* — Morgan T Barlow
(74) *Attorney, Agent, or Firm* — Knobbe, Martens, Olson & Bear, LLP

(57) ABSTRACT

An apparatus is used for growing plants or tissues under aseptic conditions. The apparatus includes a lid and a base compartment. A linking mechanism is provided for connecting the lid and the base compartment. The linking mechanism is provided with a locking mechanism, which is movable from a locked position to an un-locked position and vice-versa. In the locked position, the locking mechanism holds the lid in an abutting closed relation with respect to the base compartment. In the un-locked position, the linking mechanism is provided with means for automatically lifting the lid to an elevated-suspended position with respect to the base compartment thereby providing an access route to reach the base compartment and perform desired operations.

14 Claims, 17 Drawing Sheets

(51) Int. Cl.
  *A01G 9/16* (2006.01)
  *C12M 1/42* (2006.01)
(58) Field of Classification Search
  USPC .................................. 108/144.11, 145, 147
  See application file for complete search history.

(56) References Cited

U.S. PATENT DOCUMENTS

| | | | | |
|---|---|---|---|---|
| 3,018,586 A * | 1/1962 | Lane | ...................... | A01G 31/02 47/63 |
| 3,188,121 A * | 6/1965 | Cude | ...................... | F16L 41/08 138/99 |
| 3,768,201 A * | 10/1973 | Yoo | ...................... | A01G 31/02 47/16 |
| 3,896,595 A * | 7/1975 | Anghinetti | ................ | E05C 3/12 292/238 |
| 3,946,522 A * | 3/1976 | Schifman | ................. | A01G 9/02 47/40 |
| 3,987,924 A * | 10/1976 | Uitz | .................. | B65D 11/1873 220/4.28 |
| 4,291,494 A * | 9/1981 | Knablein | ................. | A01G 9/16 206/558 |
| 4,467,932 A * | 8/1984 | Dabich | ............... | E02D 29/1418 220/211 |
| 4,569,150 A * | 2/1986 | Carlson | .................... | A01G 9/18 47/17 |
| 4,670,398 A * | 6/1987 | Song | ...................... | A01H 4/001 220/371 |
| 4,722,160 A * | 2/1988 | Davis | .................. | E04H 13/003 47/41.01 |
| 4,739,896 A * | 4/1988 | Moss | .................. | E02D 29/1427 220/324 |
| 4,982,993 A * | 1/1991 | Okazaki | ................ | B60S 1/0405 15/250.19 |
| 4,989,367 A * | 2/1991 | Chung | ................... | A01G 31/02 47/16 |
| 5,141,866 A | 8/1992 | Levin | | |
| 5,142,819 A * | 9/1992 | Sung | ...................... | A47H 27/00 47/40 |
| 5,335,447 A * | 8/1994 | Bee | ........................ | A01G 9/225 47/17 |
| 5,462,347 A * | 10/1995 | Vogelgesang | .......... | A47B 77/10 312/247 |
| 5,469,810 A * | 11/1995 | Chiang | ................. | A01K 63/003 119/225 |
| 5,587,298 A * | 12/1996 | Horigane | ................ | C12M 41/12 366/300 |
| 5,673,810 A * | 10/1997 | Rothrock | .................. | E05F 1/02 220/264 |
| 5,946,853 A | 9/1999 | Jacobs et al. | | |
| 5,950,368 A * | 9/1999 | Bradford | ............. | E02D 29/1418 220/484 |
| 6,003,705 A * | 12/1999 | Burguieres, Jr. | ..... | B65D 88/128 220/1.5 |
| 6,690,910 B2 * | 2/2004 | Fujimoto | ............. | G03G 15/605 355/75 |
| 6,899,368 B2 * | 5/2005 | Neubrand | ................. | B60J 7/205 296/107.08 |
| 6,951,318 B1 * | 10/2005 | Petersen | ............. | E02D 29/1427 220/315 |
| 7,013,600 B1 * | 3/2006 | Bae | ........................ | A01G 31/02 47/61 |
| 7,216,459 B1 * | 5/2007 | Akkala | ................... | E02D 29/14 16/285 |
| 7,232,196 B2 * | 6/2007 | Kwon | ................... | A47B 46/005 312/402 |
| 7,731,805 B2 * | 6/2010 | Banta | ...................... | A47L 15/506 134/56 D |
| 7,797,796 B2 * | 9/2010 | Migli | ...................... | E05D 15/40 16/286 |
| 8,006,897 B1 * | 8/2011 | Douglass | ................ | G07F 19/20 109/69 |
| 8,087,532 B2 * | 1/2012 | Brown | .................. | B65F 1/0006 220/254.1 |
| 8,158,426 B2 * | 4/2012 | Wilson | ....................... | 435/297.1 |
| 8,777,338 B2 * | 7/2014 | Bunch | .................. | A47B 46/005 312/248 |
| 8,973,774 B1 * | 3/2015 | Stravitz | ..................... | B65F 1/14 220/495.06 |
| 2001/0039762 A1 * | 11/2001 | Giovannetti | .......... | E05F 1/1091 49/246 |
| 2002/0073613 A1 * | 6/2002 | Wijbenga | ................ | A01G 9/16 47/17 |
| 2005/0274076 A1 | 12/2005 | Farhadi | | |
| 2005/0279020 A1 * | 12/2005 | Hsu | ........................ | A01G 9/16 47/17 |
| 2006/0032129 A1 * | 2/2006 | Lai | ....................... | A01G 27/04 47/62 R |
| 2006/0112630 A1 * | 6/2006 | Kimes | ................... | A01G 31/02 47/62 C |
| 2006/0130608 A1 * | 6/2006 | Jones | ....................... | F16P 1/00 74/616 |
| 2006/0154642 A1 * | 7/2006 | Scannell, Jr. | ........... | A01G 9/02 455/404.1 |
| 2008/0184900 A1 * | 8/2008 | Wang | ...................... | A01G 7/06 101/35 |
| 2008/0196314 A1 * | 8/2008 | Stratten | .............. | B62D 33/0273 49/386 |
| 2009/0025287 A1 * | 1/2009 | Lee | .......................... | A01G 7/00 47/17 |
| 2009/0079215 A1 * | 3/2009 | Shirase | ..................... | E05F 1/10 296/37.12 |
| 2009/0107040 A1 * | 4/2009 | Vandenhove | .......... | A01G 1/046 47/65.7 |
| 2009/0146095 A1 * | 6/2009 | Baril | ..................... | F16K 11/207 251/331 |
| 2010/0248995 A1 * | 9/2010 | Kensy | ................. | B01F 11/0014 506/39 |
| 2010/0275518 A1 * | 11/2010 | Nakazato | ................ | E05D 5/062 49/386 |
| 2011/0010991 A1 | 1/2011 | Fujii et al. | | |
| 2011/0131885 A1 * | 6/2011 | Ajiki | ...................... | E05C 17/32 49/386 |
| 2011/0133373 A1 * | 6/2011 | Leng | ...................... | B22D 41/00 266/44 |
| 2011/0146158 A1 * | 6/2011 | Yamada | ................... | B41J 29/02 49/386 |
| 2011/0159581 A1 * | 6/2011 | Zhang | .................... | C12M 21/02 435/292.1 |
| 2011/0203172 A1 * | 8/2011 | Bailey | .................... | A01G 13/04 47/22.1 |
| 2012/0074142 A1 * | 3/2012 | Mays | ...................... | A47K 10/421 220/254.1 |
| 2012/0085036 A1 * | 4/2012 | Nishida | .................... | E05F 5/10 49/386 |
| 2012/0211493 A1 * | 8/2012 | Daggett | .................. | B01L 3/50825 220/315 |
| 2013/0076059 A1 * | 3/2013 | Zalan | ...................... | E05B 83/34 296/97.22 |
| 2013/0305603 A1 * | 11/2013 | Azoulay | ................. | A01G 31/02 47/60 |
| 2014/0043736 A1 * | 2/2014 | Onda | ...................... | H05K 5/0217 361/679.01 |

FOREIGN PATENT DOCUMENTS

WO  WO 2011077833 A1 *  6/2011  ............. A01G 31/02
WO  WO 2011079506 A1 *  7/2011  ............. A01G 31/02

* cited by examiner

BIOREACTOR VESSEL FOR LARGE SCALE GROWING OF PLANTS UNDER ASEPTIC CONDITION

FIELD OF THE INVENTION

The present invention generally relates to an apparatus for large scale growing of plants under aseptic conditions.

BACKGROUND OF THE INVENTION

The following background discussion includes information that may be useful in understanding the present invention. It is not an admission that any of the information provided herein is prior art or relevant to the presently claimed invention, or that any publication specifically or implicitly referenced is prior art.

Plant tissue culture is now a proven technology for production of large numbers of genetically identical plants, however, its widespread application to various commercially important plants is generally restricted due to the following factors, which add up to the costs:

High labor input
Need for repeated sub-culturing
Poorly controlled in vitro environment
Limited rates of proliferation in vitro
Abnormal anatomical development, resulting in poor survival of plantlets upon transplantation to soil
A labor intensive hardening step before the plant can be established in fields.
Losses due to contamination
High costs incurred on
  power consumption during autoclaving, lighting and air-conditioning,
  agar and sugar used in media preparation.

Thus, there is a need to develop efficient and dependable alternatives to achieve large scale micro propagation of plants, with minimum labor inputs. Partial automation of the micro propagation processes can serve as the most economically viable option. Liquid culture systems are necessary, considering ease in their automation. System automation could be brought about based on independently optimized processes, rather than automating the conventional procedures.

Bioreactors have traditionally been used for bacterial fermentation or for large scale production of secondary metabolites from plant cells. However, efforts to use the same for somatic embryogenesis/micro propagation could not succeed to the extent anticipated. The shear forces from fast impellers and foam formation in bubble aerated reactors caused most of the trouble (Heyerdahl et al., 1995). Many studies have been conducted to reveal the interactions between biological and physical parameters. Various guidelines for development of an automated system using bioreactors for plant tissue culture have been reviewed from time to time in the recent years (Aitken. Christie et al., 1995; Liu et al., 2003; Levin et al., 1997; Takayama and Akita, 1998; Ziv et al., 1998; Ziv, 2000). Depending on the type of explants, mode of propagation (organogenesis or embryogenesis) and the physiological and biochemical requirements of each of the stages of development, different approaches are followed for automation (Aitken-Christie, 1995). Various types of submerged culture bioreactors have been designed for generation of valuable secondary metabolites through intensive culture of organized tissues in liquid media (roots or transformed "hairy" roots, shoots, and embryos), or from undifferentiated single cells and aggregated cultures (Paek et al., 2001). Some of these include air-lift and bubble column-type bioreactors, balloon-type bubble bioreactors, stirred tank bioreactors, and ebb and flood type bioreactors. Suspension cultures of plant cells, which mimic microbial systems, constitute the primary route for secondary metabolite bioreactor operations, and the prime commercial route. These type of bioreactors have four major applications; (i) production of biomass (FIG. 2.1), (ii) production of secondary metabolites, (iii) production of enzymes, and (iv) biotransformation of exogenously added metabolites (which may be precursors in the pathway) (Leathers et al., 1994). Production of berberine from *Thalictrum minus* and *Coptis japonica* and shikonin from *Lithospermum erythrorhizon* are the two major examples of commercialized, bioreactor-based secondary metabolite production systems (Aitken-Christie, 1995). Fujita et al. (1982) reported industrialization of *Lithospermum erythrorhizon* cell suspension culture in 750-liter fermenter. Plant cell cultivation has been industrially accomplished up to a 75,000-liter bioreactor (Azechi et al., 1983; Rittershaus et al., 1989). Bioreactors devoted to mass propagation include systems for cultivation of cells, somatic embryos, or organogenic propagules (e.g., bulblets, corms, nodules, microtubers or shoot clusters) in liquid suspensions (Leathers et al., 1994). Balloon-type bubble bioreactors were developed for biomass production (Son et al., 1999a, 1999b). In most of these, the impeller of the conventional fermenter has been done away with, and both agitation and aeration are brought about by air spargers installed at their base. The shape of the vessel has also been frequently changed to shapes such as bubble shape and V-shape. Adaptation of air-lift and bubble-column bioreactors for propagation of shoot and bud clusters has provided a workable means for scale-up (Akita et al., 1994).

Though, several plants grow well in submerged culture in bioreactors, many plants fail to do so. Moreover, the survival of plantlets so obtained, is very low due to abnormal anatomy, and therefore, a separate hardening step is invariably required, unless the propagules are storage organs themselves, such as bulbs and tubers (Akita. and Takayama, 1988; Akita et al., 1994; Lim et al., 1998b; Seon et al., 2000; Son et al., 1999b; Takahashi et al., 1992; Yu et al., 2000). Because shoots are prone to hyperhydricity when grown in direct contact with liquid media, Ziv and co-workers (Ziv, 1990; Ziv, 1991a; Ziv and Ariel, 1991) used growth retardants to minimize leaf tissue development during the bioreactor proliferation stages of production. A 500 L aeration bioreactor used for shoots of *Stevia rebaudiana*, inoculated with 3 Kg fresh weight (FW) of primordia-like tissue, resulted in an exceptionally high yield (160 g/l), and subsequent re-establishment of shoots in soil (Akita et al, 1994).

Forays have also been made into development of bioreactors for non-submerged culture. Vessels have been developed that are provided with membrane rafts, or alternative supporting structure for holding the plant material in lieu of agar solidified medium (Leathers et al., 1994). The liquid nutrient medium may either be applied in the form of fine mist or may be filled in temporarily bringing about temporary immersion of the explants. Non-submerged culture type bioreactors are mainly for micro propagation and hairy root culture. Application of nutrient medium in the form of mist has been reported to be the most beneficial for culture of plantlets, as there is least amount of shear damage, and high surface area of the mist droplets result in high gaseous exchange. It has potential advantages in improving the diffusion of nutrient and gas in the region surrounding the cultured tissues. (Correl and Weathers, 1998; Correl and Weathers, 2000; Kim et al., 2001; Kim et al., 2002; Kim et al., 2003; Liu et al., 2003; Weathers and Giles, 1988). One of the earliest reports of a mist reactor with spray misting system was by Weathers and Giles (1988).

However, the work was not followed up to a scale-up stage due to various technical problems. In the same year Fox (1988) developed a system where the sprayer was replaced with an ultrasound transducer for generation of nutrient mist. In this system the transducer producing the fine nutrient mist was in direct contact with the nutrient medium. The life of the transducer was diminished by repeated autoclaving and experiments were often stopped because electrical components failed. Some of these problems were taken care of in the Acoustic Window Mist Reactor (AWMR) developed later by Chatterjee et al. (1997). They fabricated an acoustic window to separate the medium from the transducer using acoustically transparent epoxy resins initially, and later replaced it with an inexpensive polypropylene container. This system had been used for both, micro propagation: carnations (Correl and Weathers, 2000; Correl et al., 2000) as well as for hairy root culture (Woo et al., 1996). Acclimatization of the micro propagated plants could be brought about by a stepwise reduction in the relative humidity, resulting in good survival of plantlets ex vitro. Employing this technology, a bioreactor was developed by Waterford Equipment Company (New York). Herein, though initial growth of the plantlets was good, it did not last for long and necrosis set in finally, because of high concentration of residual salts on the surface of explants (Chatterjee et al., 1997).

On the other hand, application of mist in the form of spray was considered to be advantageous because of washing away of the toxins and less chances of accumulation of salts on the surface in high concentrations due to evaporation (Ibaraki and Kurata, 1991; Kurata et al., 1991). AWMR was modified by Chun et al. (1998) to develop a Modified Inner-Loop Mist Bioreactor (MILMB) of a capacity of 2.5 L. In this apparatus a concentric draught tube was provided inside the main culture vessel, which facilitated more uniform distribution of mist throughout the bioreactor volume as compared to the earlier AWMR. In an experiment, the shoots started turning brown after 25 days, most likely due to the same problem as described above (Chun et al., 2003). Woo et al. (1996) carried out hairy root culture in an AWMR, and compared the results with stirred tank and flask cultures. The increase in dry weight content in AWMR was just 4.76 times as compared to 12.9 times in stirred tank bioreactor and 21.4 times in flasks. This low growth rate in AWMR was probably due to limited nutrient supply of the air-carrier method. Because of its poor success, the prospects for scaling up of such a system for hairy root culture looked poor.

Another type of reactor used for micro propagation is chamber with provision for temporary immersion and forced ventilation, especially suitable for photoautotrophic culture. Kubota and Kozai (1992) used a vessel (2.6 L capacity) containing a multi-cell tray for keeping plants. Recently, Heo and Kozai (1999) developed a similar system using an even larger culture vessel (13 L capacity), with provision for $CO_2$ enriched forced ventilation. In this system, plantlets were cultured photoautotrophically. However, one disadvantage of these large culture vessels was that growth of the cultured plantlets usually varied due to the non-uniform distribution of $CO_2$ and other environmental factors in the culture headspace.

Similarly, Zobayed et al. (1999) developed an improved culture chamber (3.4 L capacity) with air distribution pipes to distribute the $CO_2$-enriched air uniformly. However, in a larger (20 L) culture vessel, these pipes were unable to supply $CO_2$-enriched air uniformly due to technical problems. Zobayed et al. (2000a) developed another scaled-up culture system with a larger (20 L) vessel made of acrylic. For uniform distribution of air, the chamber had a lower 2 mm high compartment with several vertical connecting tubes in between the upper and the lower chamber, directing the air flow from the air distribution chamber to the culture vessel headspace. The nutrient solution was supplied into the upper chamber with plants kept in plug trays to bring about temporary immersion. Its design did not allow flow of medium into the lower compartment. Drainage occurred along gravity.

RITA Vessel:

Yet another simple system was developed by CIRAD Biotrop, France to enable efficient culture of small sized explants such as somatic embryos. The system consisted of a small sized, two chambered main culture vessel with two ports for air supply and exit. Being small in size several vessels could be connected in a modular array, and the loss due to contamination was also restricted. The major advantage was its ability to only temporarily submerge the cultured plants, resulting in marked reduction in asphyxiation and tissue vitrification as compared to continuous immersion systems. Using this system, multiplication time could be reduced to upto half, the multiplication factor increased and the cost of production decreased to $1/10^{th}$ (Teisson et al., 1996).

Notwithstanding the amount of innovations and research in automation of plant tissue culture, there are very few automated systems actually being used on a commercial scale at present due to various problems requiring attention (Aitken Christie et al, 1995 and Chu, 1994).

The in vitro environment is controlled to achieve different objectives for both, plant quality and production economy. Simple measures have proved to be effective in several cases.

Forced Air Circulation:

The typically stagnant culture vessel headspace (with high relative humidity, unfavorable gaseous composition and little air movement) was changed using altered vessel closures, forced introduction of sterile humidified air, etc. The plantlets so generated, had enhanced growth and superior ability to survive ex vitro (Kozai, 1991a; Kozai, 1991b; Kozai et al., 1992; Kubota and Kozai, 1992; Kozai, 1991c; McClelland and Smith, 1990; Smith and McClelland, 1991; Tanaka et al., 1992).

Recycle of Nutrient Medium:

Only some of the organic and inorganic nutrients added to the medium are absorbed by the cultures, and the residual nutrients including sugar are discarded together with the gelling agent after culture in almost all the cases. Recycling of nutrients, supporting materials and energy should become important in future tissue culture systems (Kozai and Smith, 1994).

Phototrophism:

It is well known that chlorophyllous cultures, in general, have a relatively high photosynthetic capacity and that these may grow faster in many cases under photoautotrophic conditions than under heterotrophic or photomixotrophic conditions, provided that the physical and chemical environment in the vessels are properly controlled for efficient photosynthesis (Pospisilova et al., 1992). Photoautotrophic cells are known to have well-developed and physiologically active chloroplasts, in contrast to heterotrophic cells (Hazarika, 2003). Control of in vitro environment also allows elimination of sugar from the culture medium (Hahn and Paek, 2001; Kozai, 1991a; Kozai, 1991b; Kozai, 1991c; Kozai et al., 1992; Kozai et al., 1996; Langford and Wainwright, 1987). Following are the potential advantages of photoautotrophic micropropagation (Fujiwara and Kozai, 1994; Kozai and Smith, 1994):

a) Growth and development of chlorophyllous cultures in vitro.
b) Physiological and/or morphological disorders are reduced.
c) Relatively uniform growth and development.
d) Procedures for rooting and acclimatization are simplified.
e) Application of growth regulators and other organic substances could be minimized thereby reducing mutations, and phenotypic variations.
f) Loss of cultures in vitro due to contamination can be reduced.
g) Larger vessels can be used with lowered risk of contamination (Kozai, 1991c).
h) Environment control of the vessel becomes easier due to reduced microbial contamination.
i) Asepsis in the vessel is not required as long as pathogens are excluded.
j) Automation, robotization and computerization become easier.

Introduction of forced ventilation, elevated $CO_2$ and elimination of sugar from the media (Kozai, 1991a; Kozai, 1991c).

Provision of Adequate Growing Area:

The size and shape of the vessels/closures determine the limits of the growing space available to support plant growth. Besides, there may be some support at the bottom, for the plants. McClelland and Smith (1990) showed that explants routinely produced denser shoot cultures when grown in larger vessels. The quality of individual shoots was significantly better, shoot length in many species was enhanced, and size of individual leaves also increased with increase in size of the vessel. The rooting potential for micro-shoots produced in large sized vessels was also substantially improved, probably, in part, due to the enhanced leaf area and rooting cofactors present in these leaves as per their hypothesis. Photoautotrophic culture in large culture vessels with minimum risk of microbial contamination, along with forced ventilation is expected to reduce the labor costs by nearly 50% compared to conventional micropropagation systems (Kozai et al., 1999). Thus larger vessels as used in bioreactor systems are expected to promote the quality of plantlets cultured therein. However, Mackay and Kitto (1988) found that culture vessels that were excessively large also inhibited shoot length compared to the medium-sized vessels. Therefore, this parameter may need standardization for various plantlets to be propagated.

Thus, there is a need for an apparatus/bioreactor vessel that obviates the draw backs of the hitherto known prior art as detailed above.

SUMMARY OF THE INVENTION

An apparatus for growing plants or tissues under aseptic conditions is disclosed. The apparatus comprises of a lid and a base compartment. A linking mechanism is provided for connecting the lid and the base compartment. The linking mechanism is provided with a locking mechanism, wherein the linking mechanism is movable from a locked position to an un-locked position and vice-versa. In the locked position, the locking mechanism holds the lid in an abutting closed relation with respect to the base compartment. In the un-locked position, the linking mechanism is provided with means for automatically lifting the lid to an elevated-suspended position with respect to the base compartment thereby providing access route to reach the base compartment and perform desired operations.

According to an embodiment, the lid comprises of at least one nutrient medium supply channel and optionally at least one fogger to enable fogging/misting/forced ventilation within the apparatus.

According to another embodiment, the base compartment comprises of a nutrient entry port at an elevated position and a base unit to accommodate plurality of plants or seeds located below the nutrient entry port, wherein the base unit comprising holding trays and a handle attached to the holding trays.

According to yet another embodiment, the linking mechanism comprises of at least one first member having a first end and a second end. The first end of the first member is connected to a lateral surface of the base compartment at an inclined angle. At least one second member is provided, having a top end and a bottom end. The bottom end of the second member is pivotally connected to the second end of the first member at a vertical angle. At least one third member is provided, having a top and bottom end. The bottom end of the third member is pivotally connected to the bottom end of the second member and the top end of the third member connected to a lateral surface of the lid. At least one fourth member is provided, having a top and bottom end. The bottom end of the fourth member is pivotally connected to the top end of the second member and the top end of the fourth member is connected to a lateral surface of the lid.

A tank for providing nutrient material to the apparatus is provided. The tank comprises of a body containing the nutrient material and a lid with a sealing gasket positioned on top of the body and fastened to the body via a plurality of fastening devices. A plurality of sealed diaphragm valves is provided to be positioned on the lid for providing air compression/release and inlet/outlet for liquid medium and a liquid medium supply port is provided for supplying liquid medium to the tank.

A system comprises of an apparatus (as mentioned above) and a tank connected to the apparatus for providing nutrient materials (as mentioned above).

DETAILED DESCRIPTION OF THE INVENTION

Figure 1:
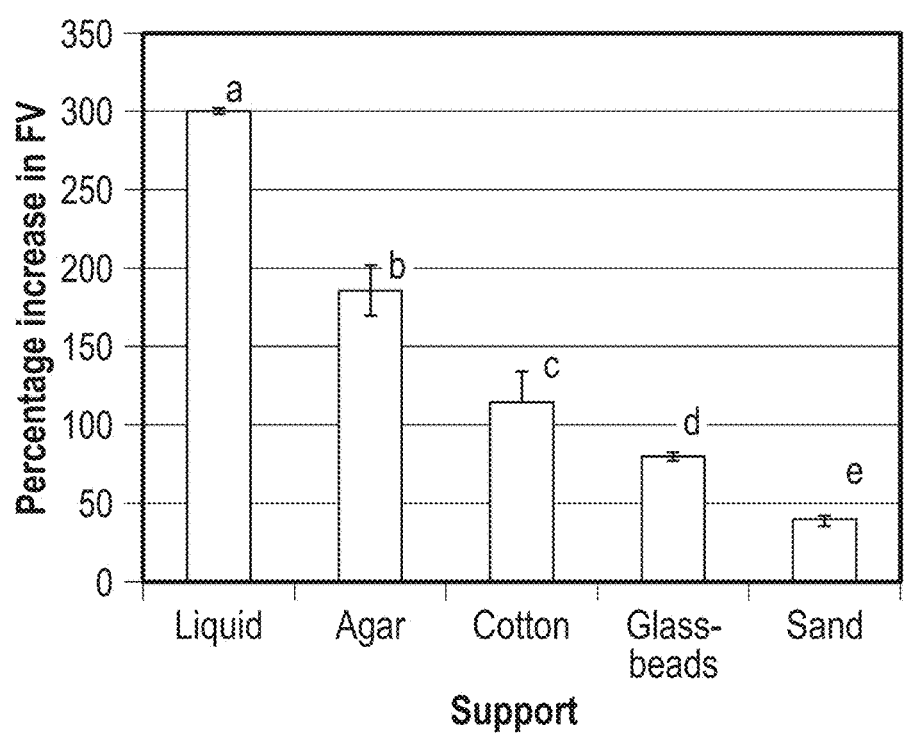
FIG. 1 illustrates the variation in percent increase in FW in liquid medium and with different support materials after 40 days, wherein the different letters above the bars shows significant difference at $P<5\%$. and the standard deviation from the mean values is also indicated in accordance with an example of the invention.

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

It will be understood by those skilled in the art that the foregoing general description and the following detailed description are exemplary and explanatory of the invention and are not intended to be restrictive thereof. Throughout the patent specification, a convention employed is that in the appended drawings, like numerals denote like components.

Reference throughout this specification to "an embodiment", "another embodiment" or similar language means that a particular feature, structure, or characteristic described in connection with the embodiment is included in at least one embodiment of the present invention. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures proceeded by "comprises . . . a" does not, without more constraints, preclude the existence of other devices or other sub-systems or other elements or other structures or additional devices or additional sub-systems or additional elements or additional structures.

Unless otherwise defined, all technical and scientific terms used herein have the same meaning as commonly understood by one of ordinary skill in the art to which this invention belongs. The apparatus, system, and examples provided herein are illustrative only and not intended to be limiting.

Embodiments of the present invention will be described below in detail with reference to the accompanying drawings.

An apparatus for large scale growing of plants under aseptic conditions is disclosed herein. The apparatus is configured to grow a large number of plants/tissues under controlled conditions of nutrient media, light, temperature, humidity and pH. The apparatus is further configured for growing a number of plants/tissues/organs for prolonged periods of time. Further, the apparatus is configured for pre-hardening of in vitro raised plants affected for better survival under ex vitro conditions.

Figure 10:
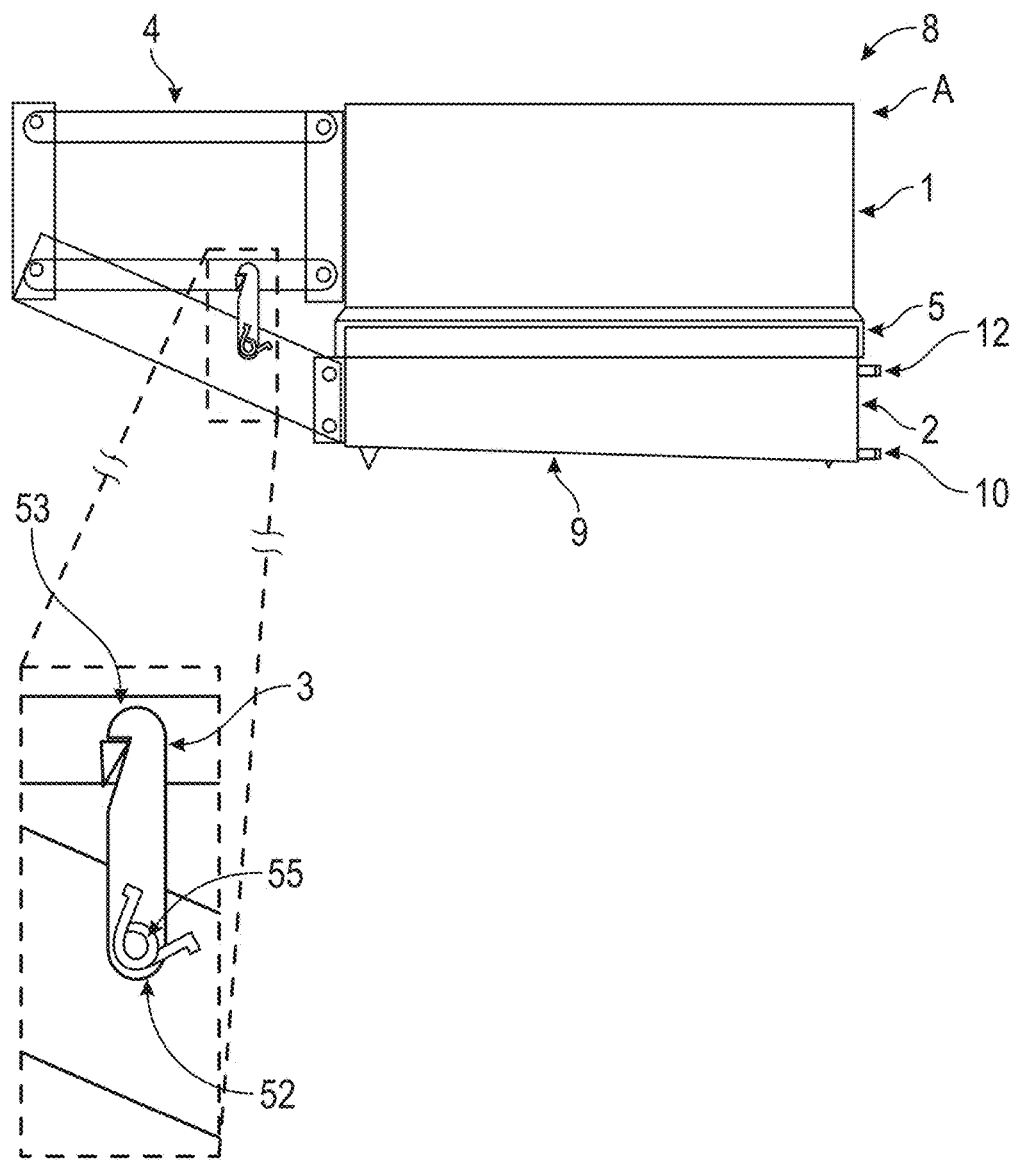
FIG. 10 illustrates various views of an apparatus for growing plants or tissues under aseptic conditions in closed position in accordance with an embodiment of the invention.
Figure 11:
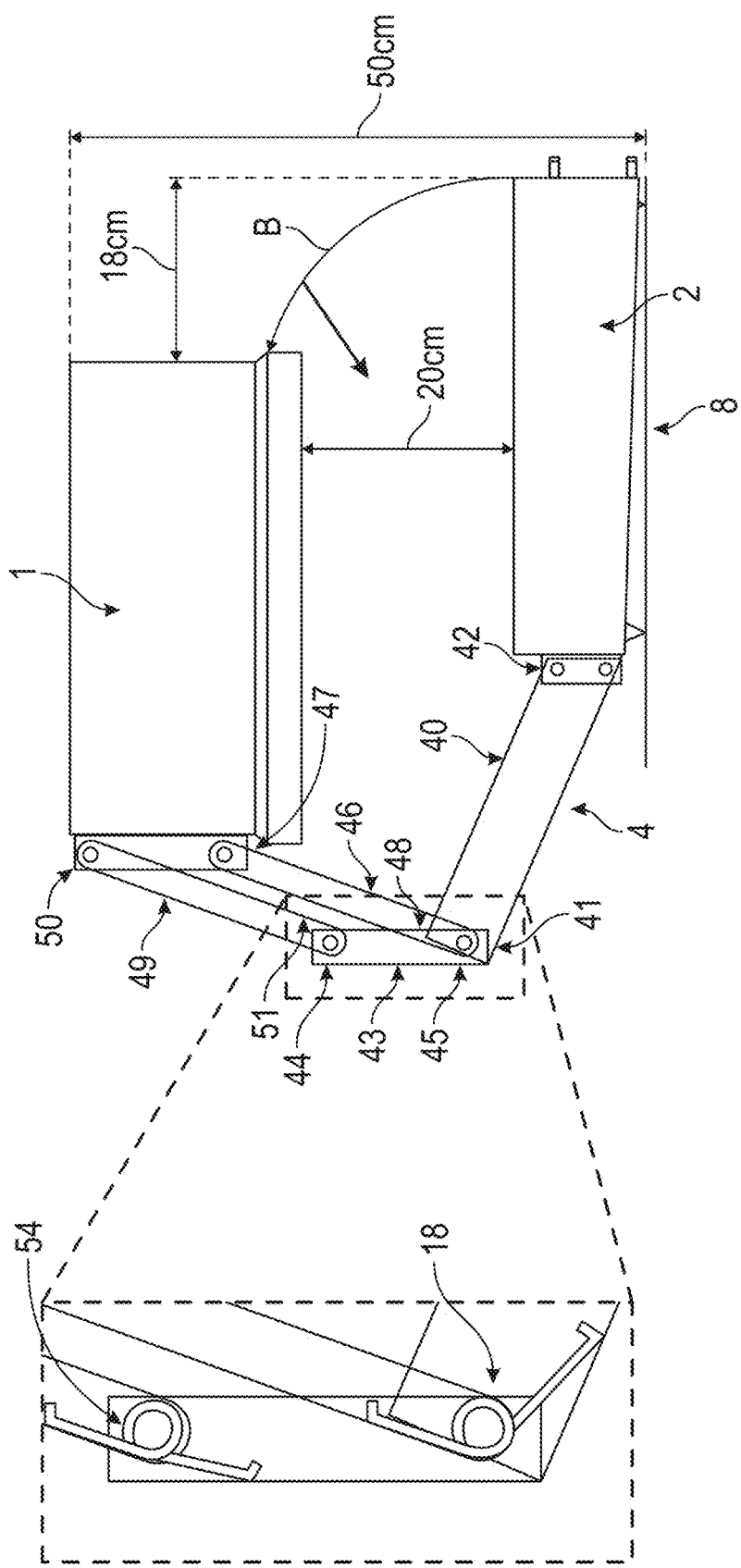
FIG. 11 illustrates various views of the apparatus for growing plants or tissues under aseptic conditions in open position in accordance with an embodiment of the invention.

FIGS. 10 and 11 illustrates different views of the apparatus 8 in accordance with an embodiment of the invention. The apparatus comprises of a lid 1, a base compartment 2 and a linking mechanism 4.

The linking mechanism 4 is provided for connecting the lid 1 and the base compartment 2. The linking mechanism is provided with a locking mechanism 3, wherein the linking mechanism 4 is movable from a locked position A (shown in FIG. 10) to an un-locked position B (shown in FIG. 11) and vice-versa. In the locked position, the locking mechanism holds the lid in an abutting closed relation with respect to the base compartment 2. In the un-locked position, the linking mechanism 4 is provided with means for automatically lifting the lid to an elevated-suspended position with respect to the base compartment 2 thereby providing access route to reach the base compartment and perform desired operations.

According to an embodiment, the means for automatically lifting provided in the linking mechanism 4 is a spring and the locking mechanism 3 is a hook latch configured with a spring. The locking mechanism is configured to hold the lid in an abutting closed relation with respect to the base compartment 2 and release the hold when the base compartment 2 is to be reached for performing desired operations. According to yet another embodiment, the spring of the locking mechanism 3 is made of steel. The linking mechanism 4 comprises of at least one first member 40 having a first end 42 and a second end 41. The first end 42 of the first member 40 is connected to a lateral surface of the base compartment 2 at an inclined angle. At least one second member 43 is provided, having a top end 44 and a bottom end 45. The bottom end 45 of the second member 43 is pivotally connected to the second end 41 of the first member 40 at a vertical angle and the top end 44 of the second member 43 is being free. At least one third member 46 is provided having a top 47 and bottom end 48. The bottom end 48 of the third member 46 is pivotally connected to the bottom end 45 of the second member 43 and the top end 47 of the third member 46 is connected to a lateral surface of the lid 1. At least one fourth member 49 is provided, having a top 50 and bottom end 51. The bottom end 51 of the fourth member 49 is pivotally connected to the top end 44 of the second member 43 and the top end 50 of the fourth member 49 is connected to a lateral surface of the lid 1.

According to an embodiment, the third 46 and fourth member 49 when connected with the lateral surface of the lid 1 may be parallel and distant from each other for effectively lifting the lid in an unlocked position B.

According to another embodiment, the means for automatically lifting the lid upwards comprises at least two springs, a first spring 18 being positioned at a pivotal connection between the first 40, second 43 and third members 46 and a second spring 54 being positioned at a pivotal connection between the second 43 and the fourth members 49.

The first, second, third and fourth members are flat bars that are rectangular in shape. The linking mechanism 4 may also be of any suitable size that can be conveniently attached to the lid 1 and base compartment 2 without affecting ease of operation. The linking mechanism 4 may be of a suitable thickness providing sufficient strength.

The linking mechanism 4 is made of any resilient material such as an alloy. The alloy can be selected from a group consisting steel, titanium, chromium, iron, copper, and any combination thereof. In the embodiment illustrated, the linking mechanism 4 is made up of steel.

The first member 40 is joined to the second member 43 and the third member 46 and fourth member 49 to the second member 43 by screws, bolts or any other joining mechanism known in the art.

According to yet another embodiment, the locking mechanism 3 comprises of a top end 53 and a bottom end 52. The bottom end 52 is connected to a surface of the first member 40 wherein the bottom end 52 may be bolted to the surface of the first member 40 thereby fixating the bottom end to the first member 40. However, the locking mechanism 3 may not be rigidly attached to the first member 40 and may be free to move in sideways direction. The bottom end 52 may comprises of a spring 55 at the pivot of the connection with the first member 40. The top end 53 of the locking mechanism 3 is connected to a surface of the third member 46 wherein the top end 53 is shaped as a hook like stricture. The top end 53 may be configured to be received by a metal staple or a ring (not shown) positioned on the surface of the third member 46 such that the top end 53 when received by the metal staple hold the lid 1 in an abutting closed relation with respect to the base compartment 2.

According to yet another embodiment, the apparatus comprises of two sets of linking mechanisms as illustrated in FIG. 10.

Figure 12:
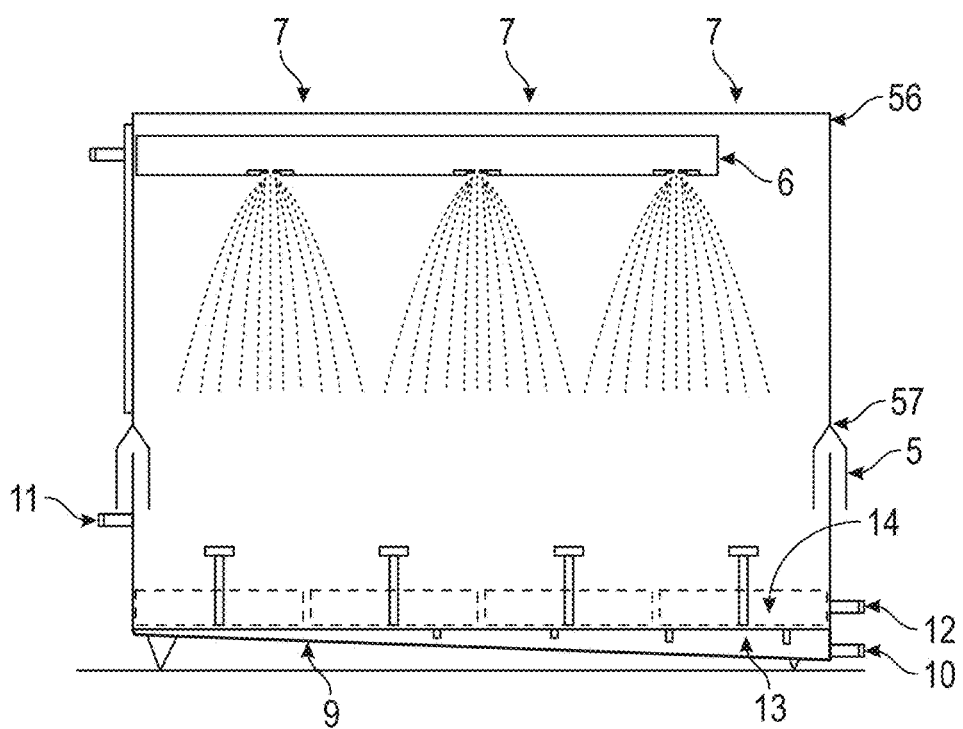
FIG. 12 illustrates a schematic diagram of the interior of the apparatus in accordance with an embodiment of the invention.
Figure 13:
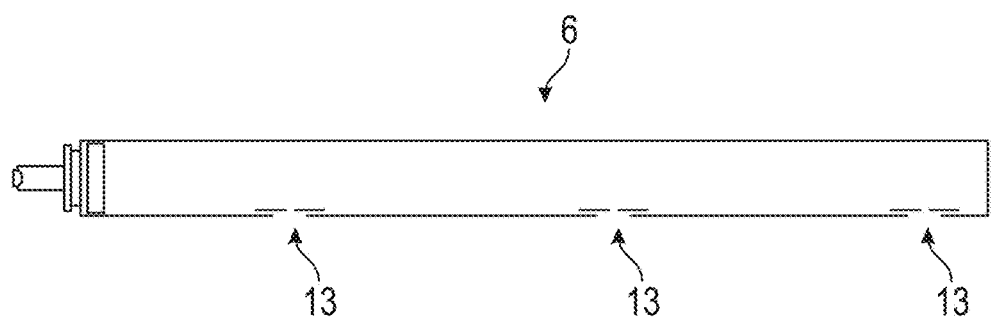
FIG. 13 illustrates a schematic diagram of a fogging channel along with positions of three foggers in accordance with an embodiment of the invention.
Figure 15:
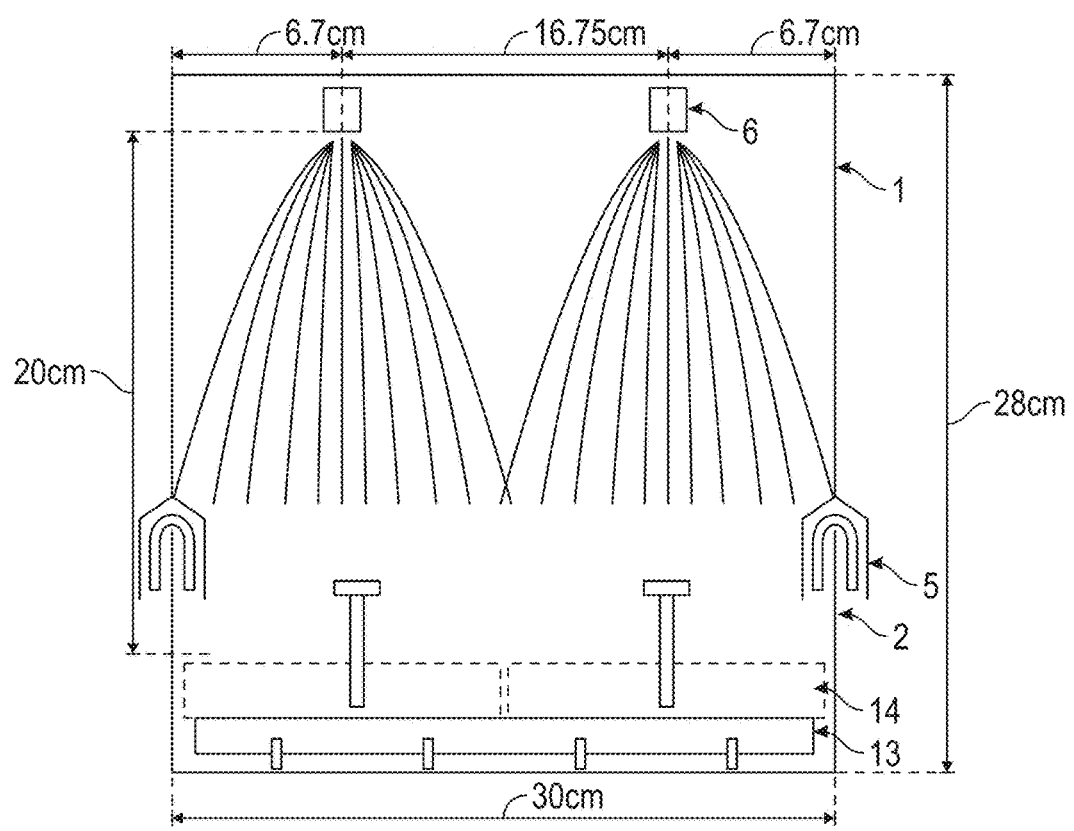
FIG. 15 illustrates a diagram showing the interior of the apparatus in accordance with an embodiment of the invention.

FIGS. 12 and 15 illustrates the lid of the apparatus in accordance with an embodiment of the invention. The lid 1 comprises of a top part 56 and a bottom part 57 with the top part 56 having a surface and the bottom surface being hollow. The top part 56 having at least one nutrient medium supply channel 6 (as illustrated in FIG. 13) fitted with at least one foggers 7 to enable uniform fogging/misting/forced ventilation within the apparatus. The foggers 7 are configured to spray nutrient materials within the apparatus.

Figure 14:
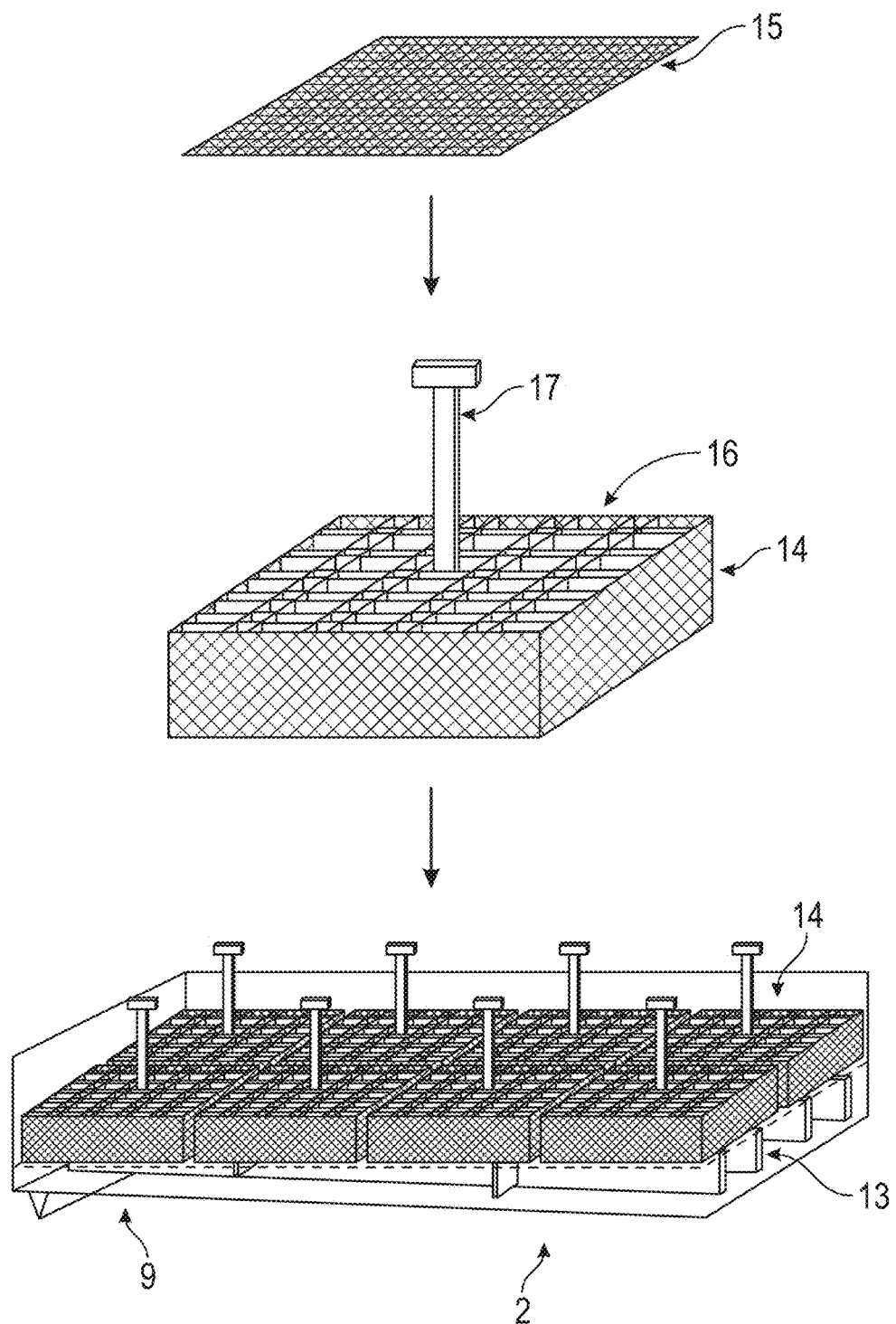
FIG. 14 illustrates various views of holding trays in accordance with an embodiment of the invention.

According to an embodiment, the lid 1 is an inverted U-shaped container made of plastic material. The diameter of the lid 1 is same as the diameter of the base compartment 2 such that the nutrient material doesn't flow out of the base compartment.

According to an embodiment, the lid 1 further comprises of an inverted U-shaped overhang enclosing a curved belt of non-absorbent pad 5 to act as a cushion for disallowing contaminants from entering into the apparatus. According to an embodiment, the non absorbent pad 5 is a cotton pad.

According to yet another embodiment, the lid 1 in the elevated position allows a minimum of 20 am vertical gap plus 10 cm horizontal displacement for unhindered operations.

According to yet another embodiment, the height of the lid is larger (21 cm) than the base compartment height (10 cm).

According to yet another embodiment, the e supply channel comprises of 3 foggers as disclosed in FIG. 12.

According to yet another embodiment, the height of the foggers fitted on the underside and below the surface of the apparatus is 20 cm for uniform distribution of the mist inside the apparatus. Three foggers are placed in each of the channel at a distance of 10 cm, 12.5 cm and 12.5 cm lengthwise inside the chamber.

According to yet another embodiment, the two supply channels are positioned in the lid with each of the three foggers on the underside of lid are kept as 16.75 cm apart leaving a gap of 6.7 cm on either side.

According to yet another embodiment, the foggers is fabricated using preferably transparent polycarbonate sheets wherein the thickness of sheets is in the range of 2.2 mm to 4.0 mm.

According to yet another embodiment, the pressure for application of nutrient medium is in the range of 22-28 psi.

FIGS. 12 and 14 illustrates the base compartment in accordance with an embodiment of the invention. The base compartment 2 comprises of a nutrient entry port 10 at an elevated position on the base compartment 2 to enable filling of the liquid medium for temporary/continuous immersion of the plants or seeds. The base compartment 2 having a base unit 13 to accommodate plurality of plants or seeds below the nutrient entry port 10, wherein the base unit 13 comprising of holding trays 14 and a handle 17 for removal of holding trays 14.

According to yet another embodiment, the holding trays 14 are made of autoclavable and Netlon material mesh.

According to yet another embodiment, the holding trays 14 are provided with cross plates made of Poly methyl pentene (TPX®) transparent sheets for making cells in which the plants/tissues could be kept in an upright position.

According to yet another embodiment, the preferred dimensions of the holding trays 14 is length 14 cm, width 10.5 cm and height 3 cm.

According to yet another embodiment, the apparatus can hold up to 8 holding trays as illustrated in FIG. 14.

According to yet another embodiment, the floor of the base of the apparatus is made inclined at an angle to enable complete drainage through a drain port at the lower side.

According to yet another embodiment, the locking mechanism is made out of autoclavable, corrosion resistant material preferably UV stabilized poly-carbonate with height complementary to the inclination of the floor of the base unit to ensure all holding trays are at a constant level horizontally for allowing equal submerging of the explants during simple medium filling.

The base compartment comprises of a first drain port 10 at an elevation lower than the holding tray 14 to enable drainage of the liquid nutrients. The base compartment 2 further comprises of a second drain port 12 at an elevation higher than the first drain port 10 and the holding trays 14 to ensure sufficient submersion of the lower parts of the plants as per experimental requirements. According to an embodiment, the base unit 13 comprises a support structure for locating the holding trays 14 at a predetermined position. The floor of the base unit 13 is made at an angle to enable complete drainage through the first drain port 10. The angle of the floor is inclined with respect to a horizontal axis.

According to yet another embodiment, the base compartment 2 is a rectangular box made of plastic.

According to yet another embodiment, the floor of the base unit 13 has enough space to accommodate the plurality of explant holding trays 14 and provided with cross plates 16 capable of withstanding high temperatures and pressures during autoclaving for making cells for holding plants/organs/tissues to be grown.

According to yet another embodiment, the base unit 13 is provided with the handle 17 such as a stalk for ease in handling and holding the trays.

According to yet another embodiment, the sterile cultures are aseptically inoculated in the explant holding trays. The apparatus is opened inside the laminar air flow by releasing its lock.

According to an embodiment, the apparatus 8 is a bioreactor vessel.

According to another embodiment, the apparatus 8 is made of any non-corrosive, transparent moldable material capable of withstanding high temperatures and pressures during steam sterilization preferably polycarbonate and similar materials.

According to yet another embodiment, the height, width, and depth of the apparatus are 28 cm×45 cm×30 cm respectively.

Figure 16:
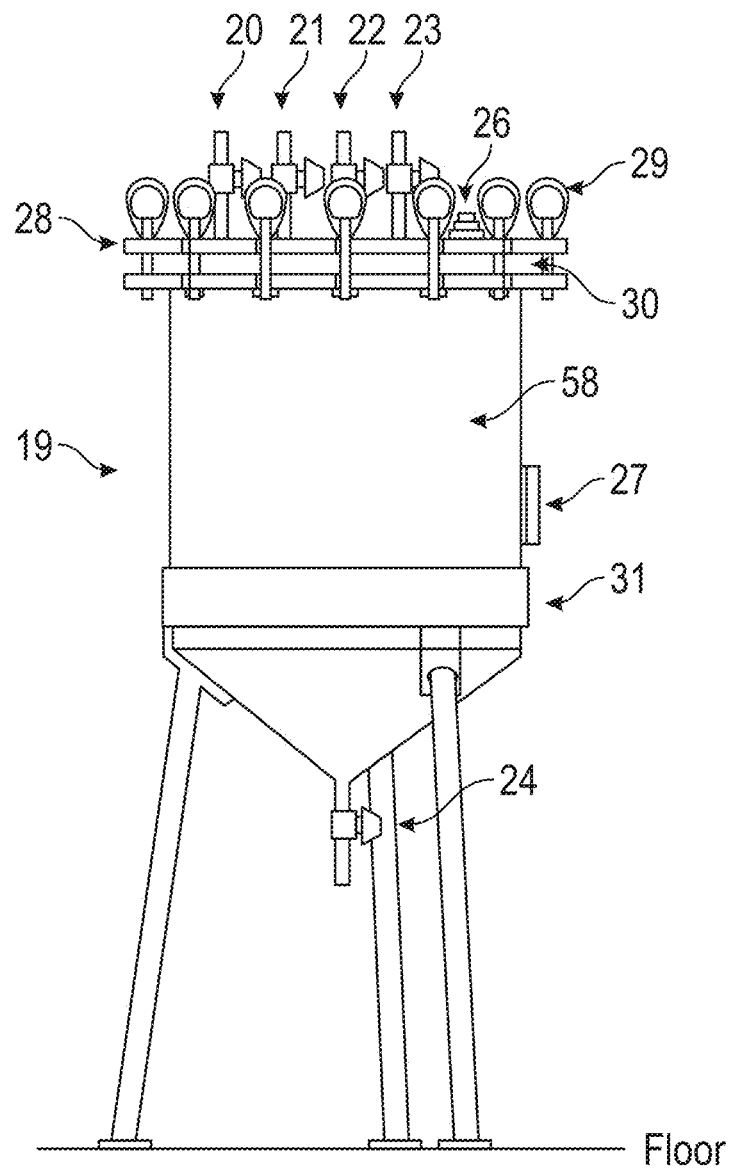
FIG. 16 illustrates a frontal and top view of a tank in accordance with an embodiment of the invention.
Figure 16:
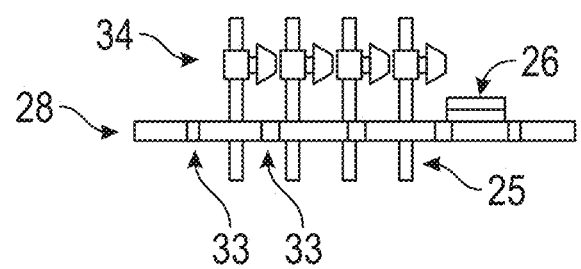
Figure 17:
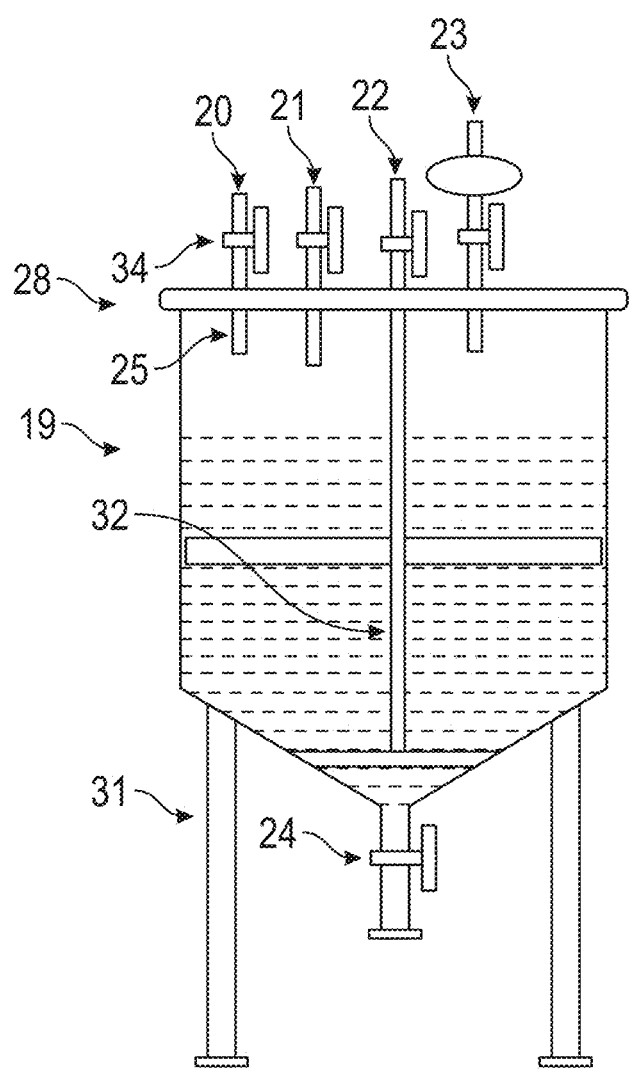
FIG. 17 illustrates a schematic view of the tank in accordance with an embodiment of the invention.

FIGS. 16 and 17 illustrates a tank in accordance with an embodiment of the invention. The tank 19 is configured for providing nutrient material to the apparatus, comprising of a body 58 containing the nutrient material. A lid 28 is provided to be sealed with a sealing gasket 23 positioned on top of the body 58 and fastened to the body 58 via a plurality of fastening devices. According to an embodiment, the fastening device is a swing-screw 29. A plurality of sealed diaphragm valves 20, 21, 22 and 23 is provided to be positioned on the lid. The diaphragm values 20, 23 are provided for air compression/release and diaphragm values 21, 22 are provided for inlet/outlet for liquid medium. A liquid medium supply port 32 is provided for ensuring supply of liquid medium to the tank 19.

According to an embodiment, the tank 19 is connected to the apparatus 8 by means of a pipe or a hose or any other means for transferring nutrient materials from one vessel to the other vessel.

According to another embodiment, the tank 19 further comprises of an outlet 24 ensuring complete draining of the content from inside the tank 19.

According to yet another embodiment, the tank 19 is made of non-corrosive stainless steel metal to enable steam sterilization and to withstand pressurization during operation.

According to yet another embodiment, the capacity of the tank 19 is optimized as 30 liters; with 20 liters of nutrient medium and 10 liters for compressed air to be used for misting and also for ventilation of the apparatus using an appropriate air pump.

According to yet another embodiment, the lid 28 of the storage tank 19 is fixed to the body by swing screws or nuts and bolts to avoid any leakage.

According to yet another embodiment, the lid 28 of the storage tank 19 is provided with an autoclavable ring of gasket which is made of neoprene or silicone rubber.

According to an embodiment, the tank 19 is positioned over a tripod stand 29.

According to yet another embodiment, the tank 19 is provided with two air tight glass windows 26, 27, one each in the lid 28 and in the vertical wall of the tank 19 for illumination with any suitable external light source to monitor any contamination.

According to yet another embodiment, the apparatus 8 is aseptically connected to a system of tanks, tubing's, pumps, valves, filters, flow meters, disinfection units for regulated supply sterile nutrient medium/forced sterile air.

According to yet another embodiment, external illumination is provided to the apparatus on the culture benches through the lights fitted on them. The setup may be operated by supplying the appropriate nutrient medium/forced air as per the experimental plan, for a prolonged period. After completion of the experiment/achieving desired growth the apparatus can be aseptically removed from the rest of the system, opened in sterile laminar air flow to remove the cultured plant material aseptically, cleaned and prepared for the next cycle of culture.

According to yet another embodiment, one or more apparatus are connected in parallel with the tanks.

A system is disclosed. The system comprises of an apparatus 8 as disclosed above and a tank 19 connected to the apparatus 8 for providing nutrient materials as disclosed above. The system provides a holistic environment wherein the apparatus 8 for growing plants or tissues under aseptic conditions is connected to a storage tank 19 for providing nutrient material to the apparatus.

EXAMPLES

The following examples are given by way of illustration and therefore should not be construed so as to limit the scope of the invention.

The explants for experimented work were taken from the aseptic cultures of Asiatic lilium (*Lilium longiflorum* var. *Pollyanna*). The cultures were maintained on Murashige and Skoog (MS/1962) medium supplemented with BA (1.25 mg/l), IBA (2 mg/l), NAA (0.5 mg/l), sucrose (3%, w/v) and agar (0.8%, w/v) and pH was adjusted to 5.8 prior to autoclaving. The cultures were incubated at a photosynthetic photon flux density (PPFD) of 70±5 umolm$^{-2}$ s$^{-1}$ from cool, white, fluorescent lamps in a 24 h light/dark cycle. The bioreactor, standardization with respect to optimum. MS salt strength and suitability of liquid media, role of growth retardants such as paclobutrazol (PBZ) and ancymidol (ANC) for their potential to improve desirable features of plants and their better survival, pH of the medium, sterilizing agents such as sodium hypochlorite, Plant Preservation Mix (PPM from School of Agriculture, University of Wisconsin, USA), effect of anti-biotics such as aureomycin, carbenicillin, cefotaxime, kanamycin, nalidixic acid, penicillin, sporidex and streptomycin used at concentrations ranging from 0-500 mg/l. Depending upon the size of each cluster of *Lilium* plantlets, 12 (Large) to 63 (small) explants could be placed in one holding tray and a total of eight trays could fit in each bioreactor.

The suitability of the bioreactor for growing large scale Hums under aseptic conditions, their growth performance under misting as well as temporary immersion at the basal ends only by controlling the medium entry into the bioreactor appropriately was studied by employing two bioreactors connected in parallel in a single set up. In one bioreactor, the nutrient medium was applied for 10 seconds in the form of a mist, four times a day. Whereas, in the second bioreactor, medium was applied 4 times a day by simple filling in the trough of the bioreactor until the lower ends of plantlets were partially submerged. In both the cases, the medium was drained out immediately. Thereafter, the growth parameters were measured, and percent increase in total leaf area (TLA), fresh weight (FW), bulb number (B#) and total bulb volume (TBV) were calculated. For measurement of the growth parameters, 9 plantlets from the explants holding trays were randomly selected. Three such trays were treated as three replicates and data was analyzed using complete Randomized Design (CRD-one factor). Besides, data on dry weight to FW ratio, number of bulblets generated per unit weight of biomass, percentage of leaf surface area under stomata, chlorophyll content, starch content, wax content and photosynthetic ability were also calculated.

Further in order to find out the economic viability and because expenses on sucrose constitute a major component of media, experiments were also conducted to test the photosynthetic growth ability of *Lilium* plantlets which were then evaluated for ex vitro survival and growth in the specially created hardening facility. A comparison of growth of plantlets when exposed to liquid medium supplemented with 3% (w/v) sucrose or the one without any carbohydrates upto 40 days were studied and all the growth parameter as described above were calculated.

Example I

It was found that the use of any support system in the medium resulted in a significant drop in the growth rate as inferred by monitoring the percent increase in FW of the plantlets in each of the cases. FW increase was approximately 301% for liquid medium alone, 186% for agar solidified medium, 112% for cotton as support, 78% for glass-beads as support, and 38% for sand Thus, it could be easily deduced that the growth of *Lilium* plantlets was best in liquid medium without any need of supporting material (FIG. 1).

Example 2

Figure 2:
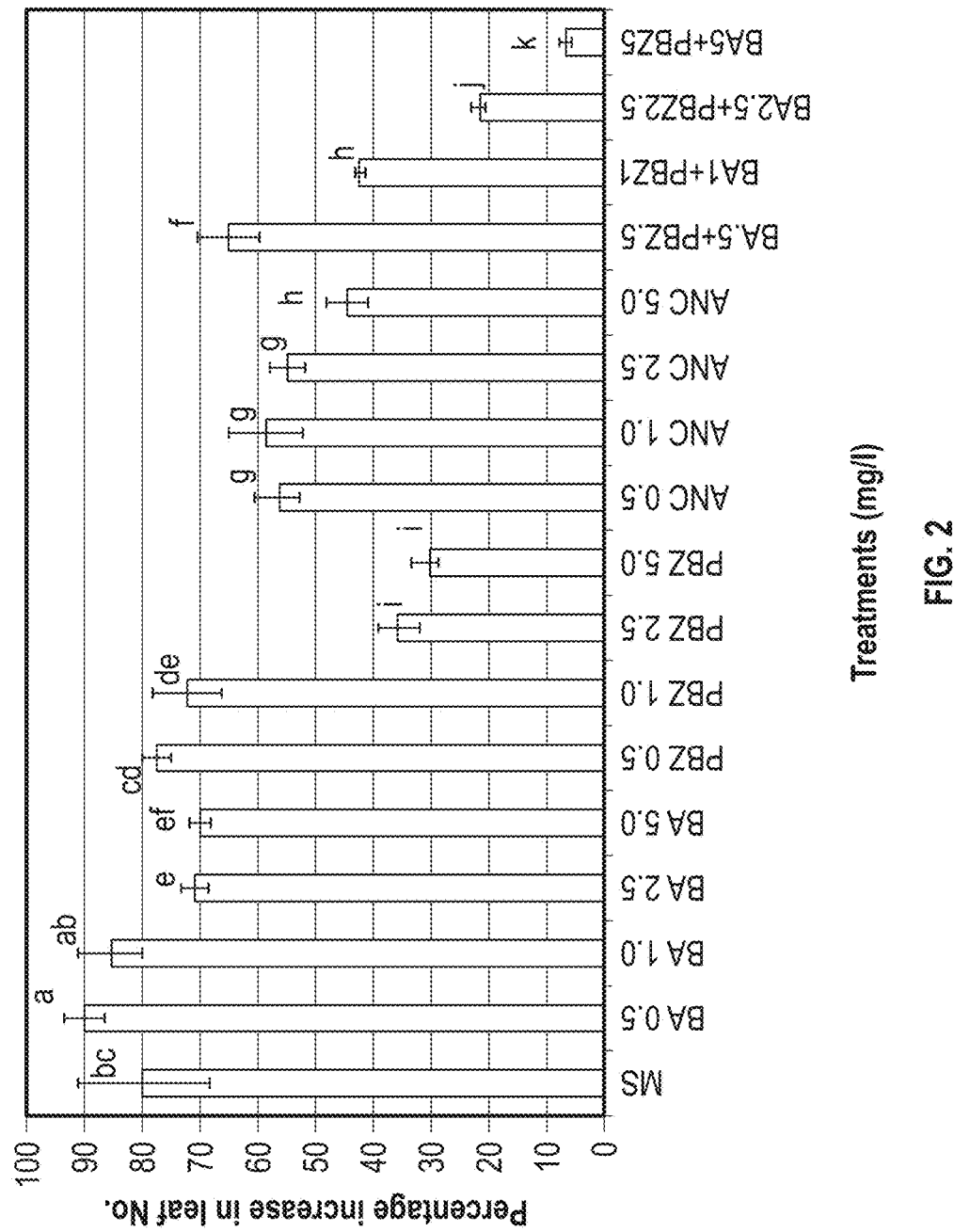
FIG. 2 illustrates the variation in percent increase in the number of leaves with various growth regulator treatments after 40 clays, wherein the different letters above the bars showed significant difference at $P<5\%$ and the standard deviations from the mean values are also indicated in accordance with an example of the invention.

The percent increase in the number of leaves per plantlet was maximum (90%) in plantlets grown on media with BA 0.5 mg/l (FIG. 2). It was only slightly affected by application of growth retardants at lower concentrations (PBZ 0.5 and 1.0 mg/l, ANC 0.5, 1.0 and 2.5 mg/l; PBZ 0.5 mg/l along with BA 0.5 mg/l), but decreased sharply with increase in their concentrations (PBZ 2.5 and 5 mg/l; ANC 5.0 mg/l; PBZ along with BA at all concentrations above 0.5 mg/l) as compared to that of plantlets grown on control medium and on medium with BA alone at various concentrations. Thus, it shows that growth retardants can be used at low concentrations (0.5 and 1.0 mg/l), without manifestation of any adverse effects on the leaf formation in vitro.

Example 3

Figure 3:
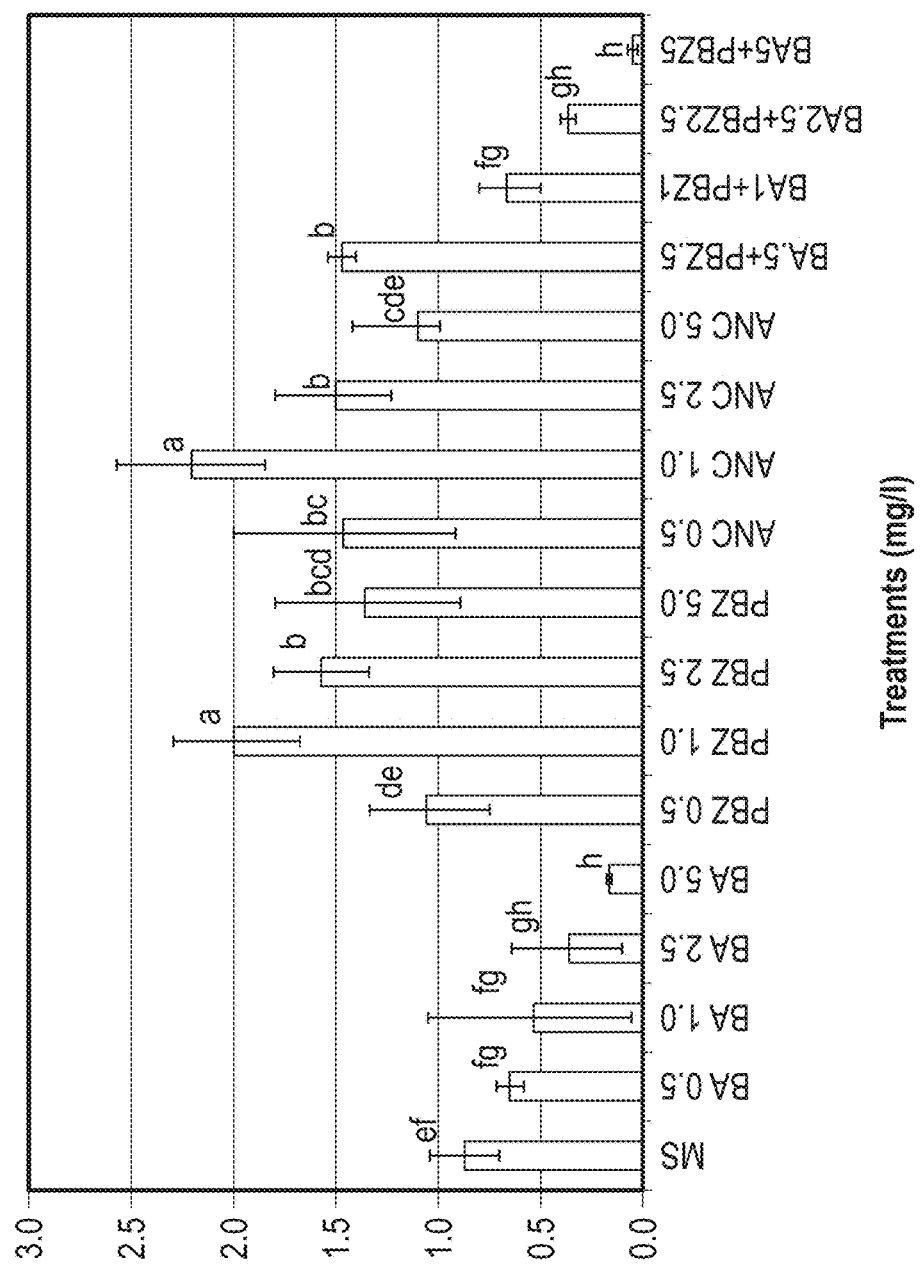
FIG. 3 illustrates the variation in percent increase in the number of roots per bulb, with various growth regulator treatments after 40 days, wherein the different letters above the bars showed significant difference at $P<5\%$ and the standard deviation from the mean values is also indicated in accordance with an example of the invention.

Treatment of plantlets with growth retardants significantly promoted the number of roots per bulblet, as compared to the plantlets raised on control medium or medium supplemented with BA alone at all the concentrations tested. The roots showed prolific growth and remained normal on low concentrations of growth retardants (0.5 mg/l, 1.0 mg/l), but these turned stout and slightly swollen when higher doses (2.5 mg/l and 5 mg/l) were employed. Best root induction was discerned in response to PBZ at 1.0 mg/l (FIG. 3) and ANC at 1.0 mg/l.

Example 4

Figure 4:
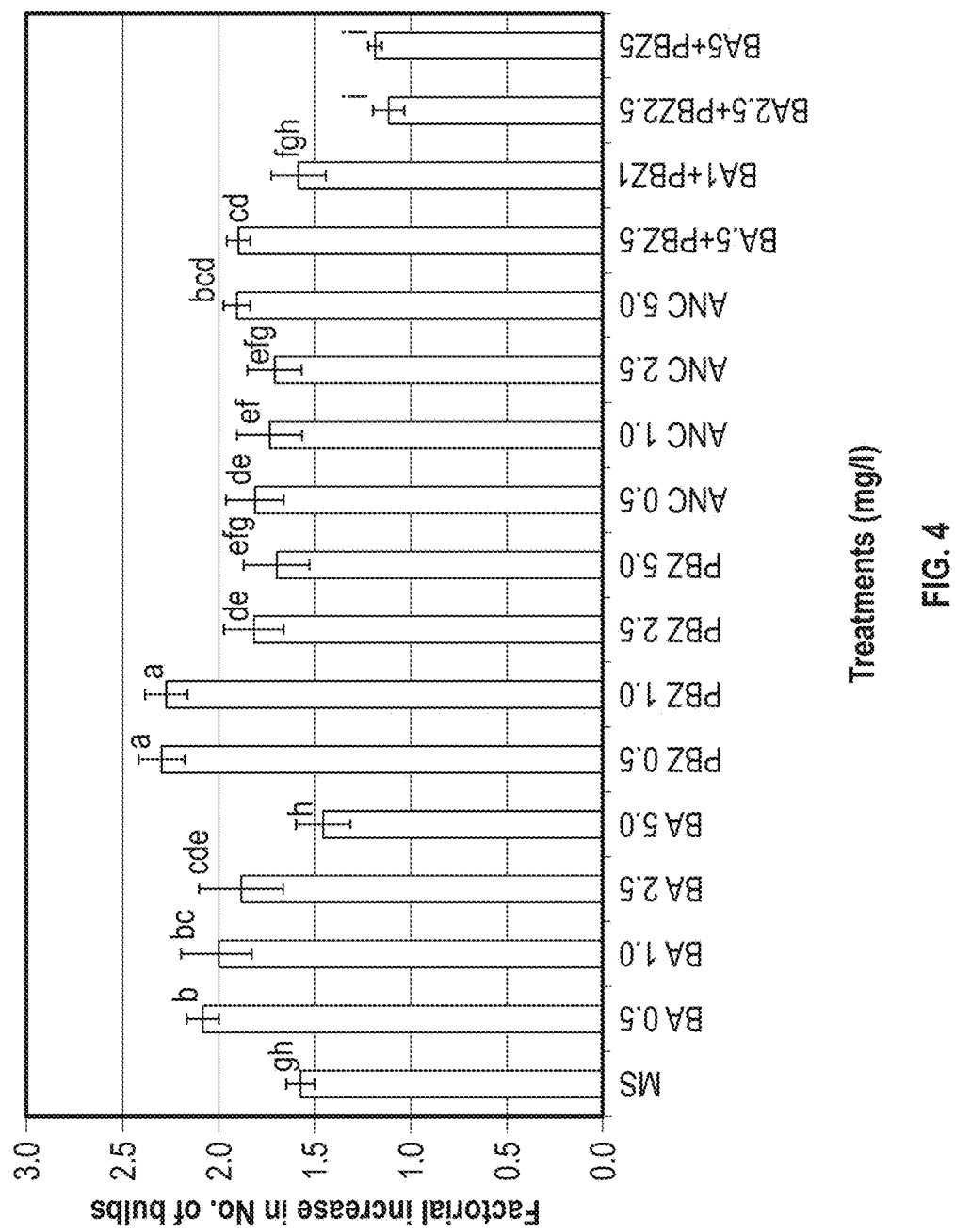
FIG. 4 illustrates the variation in factorial increase in the number of bulblets, with various growth regulator treatments after 40 days, wherein different letters above the bars showed significant difference at P<5% and the standard deviation from the mean values are also indicated in accordance with an example of the invention.

The factorial increase in the number of bulblets, i.e., the degree owf proliferation, was promoted by presence of either the cytokinin BA; or the growth retardants PBZ or ANC. However, at higher concentrations of PBZ along with BA (2.5 or 5 mg/l each), an inhibitory effect on proliferation was observed (FIG. 4). The maximum increase, 2.31 fold, was in the plantlets treated with PBZ (0.5 mg/l), followed by 2.27 fold for the ones treated with PBZ mg/l). This implied that the growth retardants could be used at low concentrations (0.5 mg/l, 1.0 mg/l) for *Lilium* propagation to bring about bulblet formation.

Example 5

Figure 5:
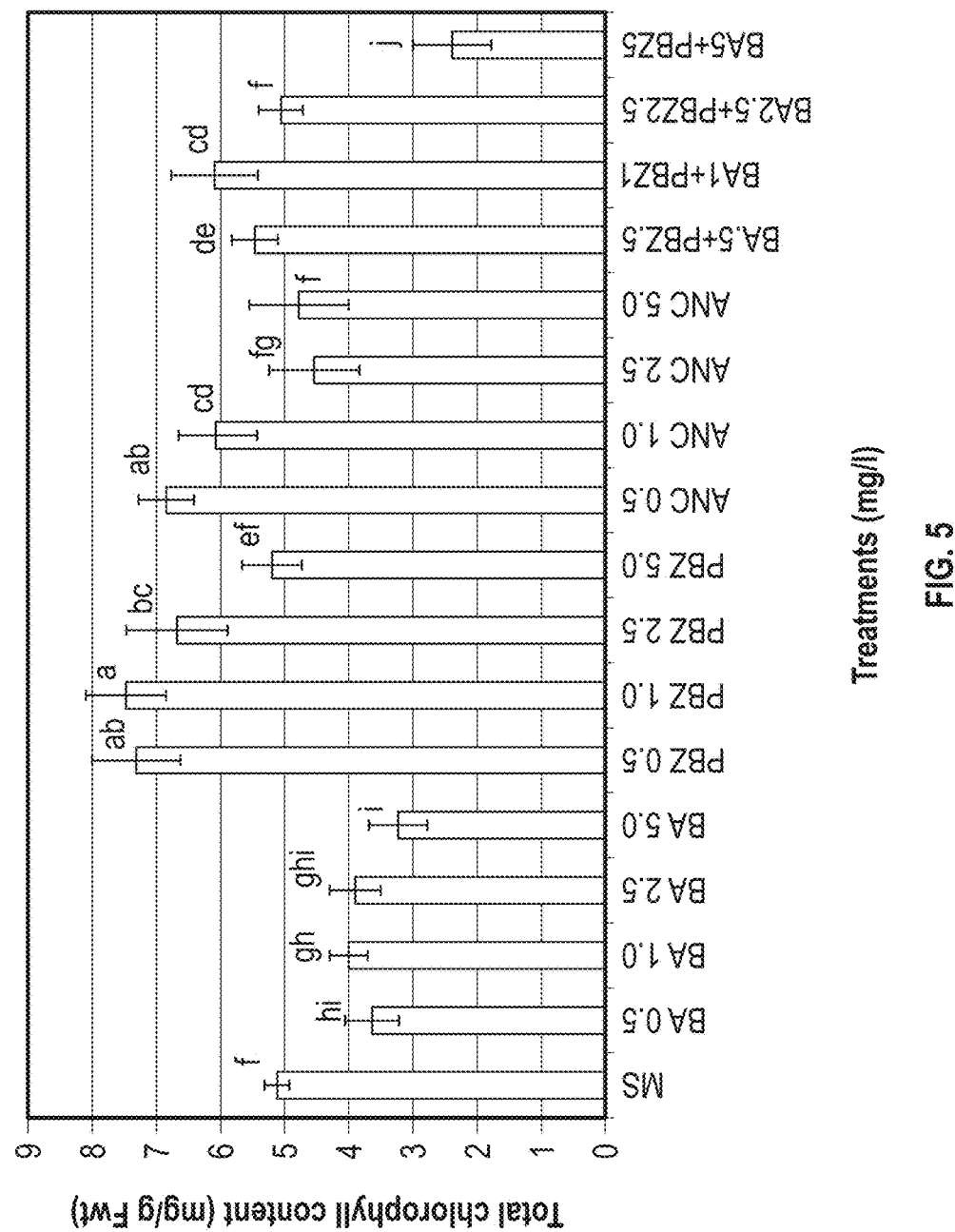
FIG. 5 illustrates the variation in chlorophyll content (mg/g FW) with various growth regulator treatments after 40 days, wherein the different letters above the bars showed significant difference at P<5% and the standard deviation from the mean values is also indicated in accordance with an example of the invention.

The chlorophyll content showed a significant increase when plantlets were cultured in the presence of growth retardants at low concentrations (0.5 and 1.0 mg/l) than at higher concentrations (2.5 and 5 mg/l) (FIG. 5). The chlorophyll content of the plantlets cultured on media with BA alone at various concentrations was lower than that of even the control plantlets, indicating their unsuitability for producing plantlets with higher chlorophyll content. The results indicated that application of growth retardants was suitable for generation of plants with higher chlorophyll content in their leaves, which is important for attaining autotrophy upon ex, vitro transfer.

Example 6

Figure 6:
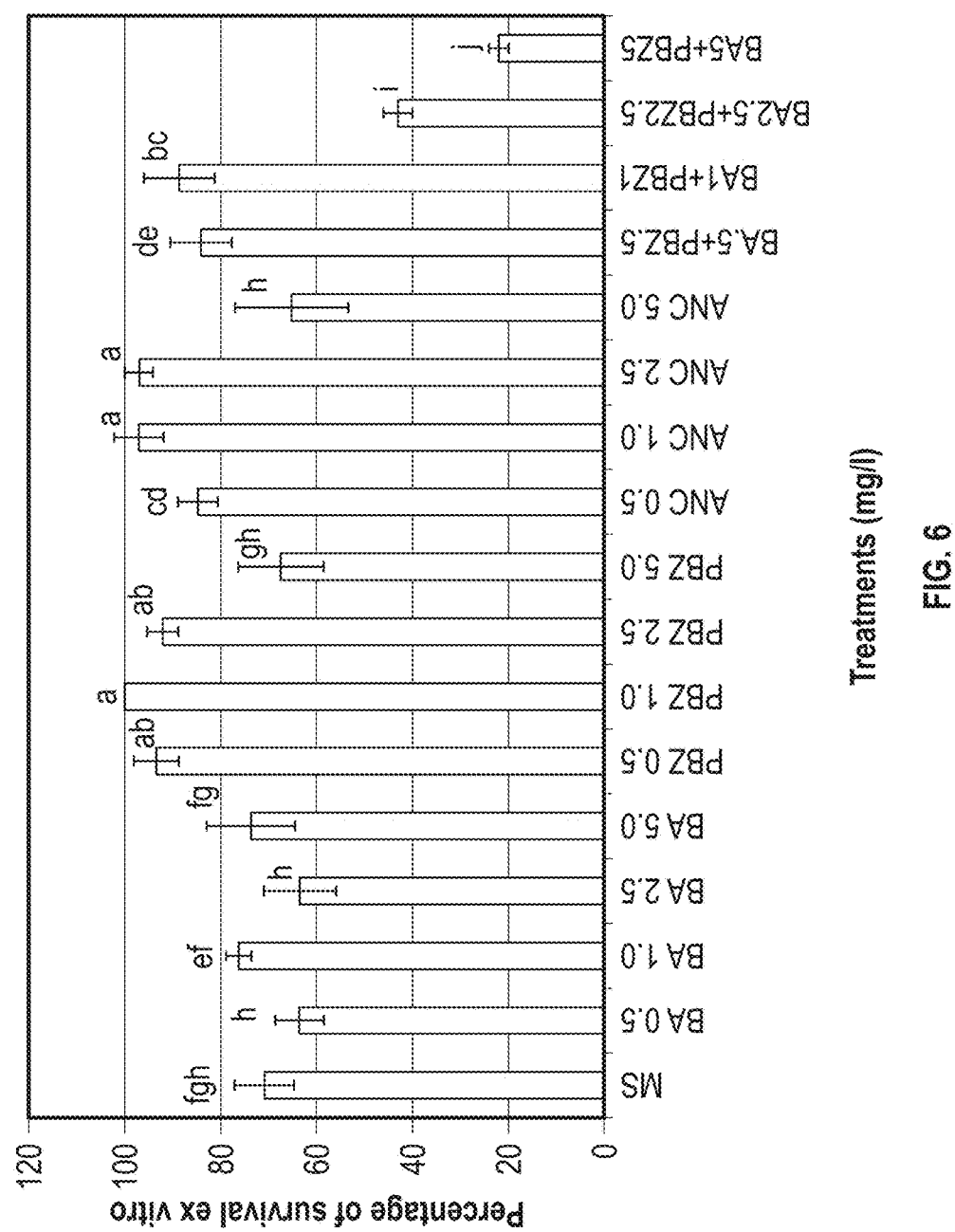
FIG. 6 illustrates the percentage of survival of plantlets raised through various growth regulator treatments of 40 days, wherein the different letters above the bars showed significant difference at P<5% and the standard deviations from the mean values are also indicated in accordance with an example of the invention.

Upon 40 days of ex vitro transfer, the plants with prior in vitro treatment with growth retardants (0.5 to 2.5 mg/l), exhibited better survival and good growth (FIG. 6). Ex vitro survival was considerably reduced for plantlets cultured in the presence of higher concentrations (2.5 or 5.0 mg/l) of PBZ along with BA. Maximum survival percentage (100%) was observed for plantlets raised on medium with PBZ (1.0 mg/l). Thus, PBZ (1 mg/l) treatment alone was found to be the best for generation of good quality plantlets showing better adaptation and highest survival upon ex vitro transfer.

Example 7

Figure 7:
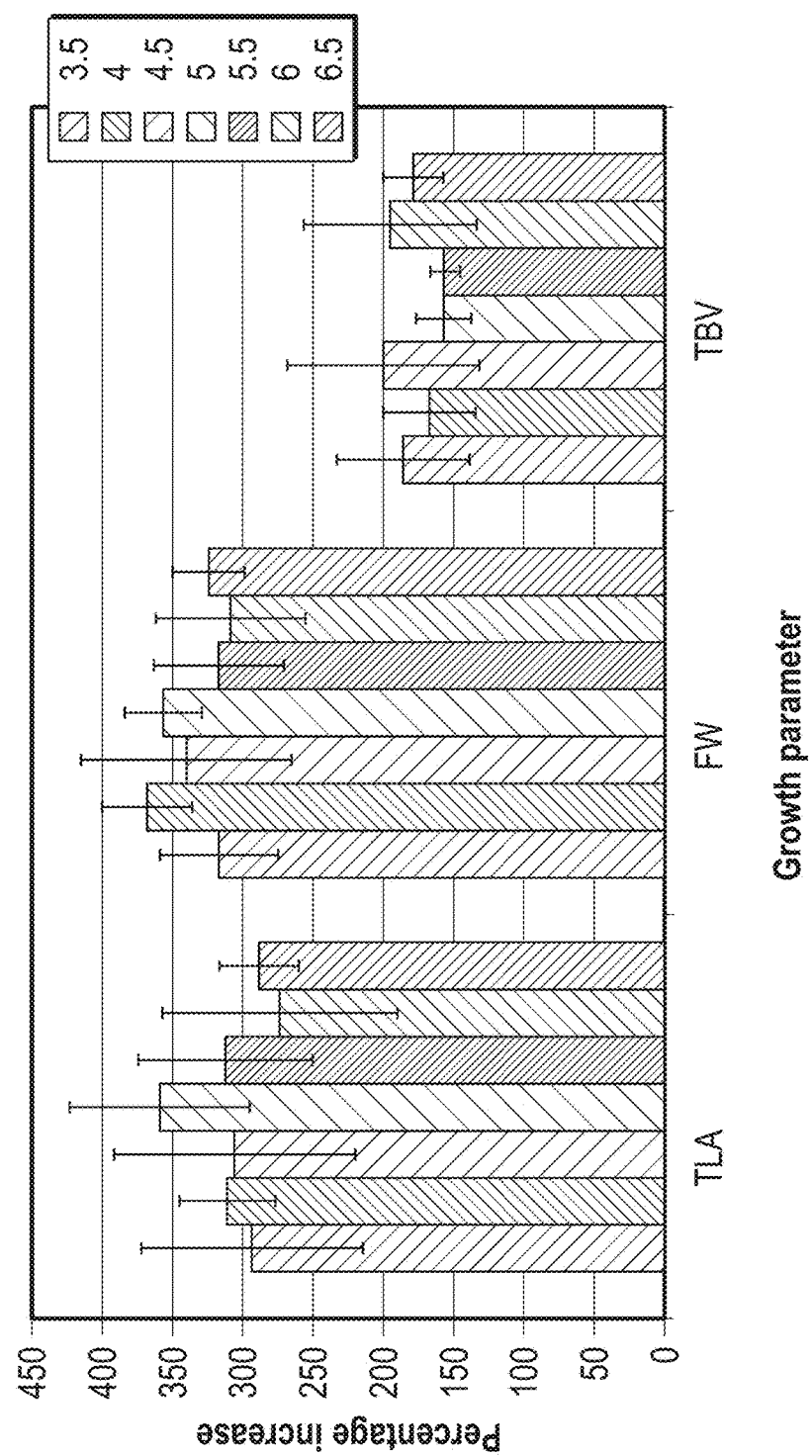
FIG. 7 illustrates the influence of medium pH upon percent increase in TLA, FW, TBV after 40 days. Differences between response to different pH were insignificant at P<5%, wherein the standard deviations from the mean values are also indicated in accordance with an example of the invention.

The pH of the media remained almost unchanged after autoclaving in more acidic samples, viz., 3.5, 4, 4.5, 5, 5.5, but decreased for the higher initial pH values (FIG. 7). Media with initial pH of 6 and 6.5 fell to 5.5 and 5.9, respectively. After inoculation, within 2 to 4 days, irrespective of the starting pH, the final pH of the medium stabilized at approx. 4.7 and continued to remain so without having any adverse effect on the plantlets as recorded after 40 days of culture. Further, there were no significant variations among the various growth parameters, irrespective of the initial pH of the medium.

Example 8

Two experiments were conducted to study the efficacy of sodium hypochlorite (NaOCl) in controlling the growth of the microbes, and to study the tolerance in plants, at various concentrations. The following results were observed:

Expt-A:

Influence of strength of active chlorine upon efficacy in controlling the contaminating microbes.

0 to 80 ppm: Contaminant microbes could grow in all the nine flasks.

150 ppm: No contamination 300 ppm: Only one of nine flasks got contaminated.

600 and 1200 ppm: No contamination.

From this result; it could be inferred that a concentration of sodium hypochlorite equal to or above 150 ppm is required to have some control upon the growth and proliferation of the contaminating microbes.

Expt-B:

Influence of strength of active chlorine upon growth of *Lilium* plantlets.

In the broad range experiment, the plantlets grew well in the concentration range 0 (Control), 10, 20, 40, 80, 150 ppm but their growth was adversely affected at concentrations of 300 ppm and above. Based on this result a narrow range trial was designed with active chlorine concentrations 0 (Control), 100, 130, 160, 190, 220, 250, 280, 300 ppm. The observations of the various growth parameters and calculation of the comprehensive absolute and differential indices are summarized in the Table 1 below.

The various sodium hypochlorite (active chlorine concentration) treatments and the control were sorted according to the absolute index. The differential index also exhibited almost a similar pattern.

It was observed that the active chlorine concentrations 100 ppm, 130 ppm, 160 ppm did not have any adverse effect as compared to control. As the concentration of the available active chlorine was increased above 190 ppm, there was a sudden drop in the growth of the plantlets. Now collectively from the results of the above two experiments, it was concluded that an active chlorine concentration in the range from approximately 150 ppm to 200 ppm could be used to minimize the risk of contamination, without adversely affecting the quality of the *Lilium* plantlets.

TABLE 1

| NaOCl | Percent increase in | | |
|---|---|---|---|
| | Total Leaf area | Fresh weight | Total Bulb Volume |
| 0 ppm | 261.76 | 394.03 | 365.10 |
| 100 ppm | 273.77 | 485.10 | 404.12 |
| 130 ppm | 229.87 | 472.77 | 433.01 |
| 160 ppm | 196.82 | 403.14 | 474.02 |
| 190 ppm | 153.86 | 375.44 | 487.34 |
| 220 ppm | 123.27 | 289.19 | 259.33 |
| 250 ppm | 109.27 | 277.09 | 385.71 |
| 280 ppm | 105.32 | 249.47 | 267.26 |
| 300 ppm | 15.90 | 135.56 | 346.90 |

Example 9

The bioreactor raised plantlets, while increase in TLA and FW were 365% and 419%, increase in their TBV was only 187% (Table 2). Besides, starch and, thy weight contents of the bulbs were also less. Upon ex vitro transfer, the plantlets grown on agar solidified medium in jars inspite of their smaller and variable size started reviving sooner than the plantlets raised in the bioreactor, as measured by the TLA per plant and calculation of percentage of its increase. The leaves of the plantlets raised in the bioreactor shriveled, and growth was reduced until the development, of new leaves.

TABLE 2

Comparison of growth parameters of plantlets raised in bioreactor vis-à-vis those raised in jars

| | Jar-liquid | Bioreactor |
|---|---|---|
| Increase in TLA (Mean) | 323% | 365% |
| Increase in FW (Mean) | 363% | 419% |
| Increase in TBV (Mean) | 183% | 187% |
| Total chlorophyll content (mg/g) | 5.82 | 6.14 |
| Starch content in bulbs (%; w/w) | 3.09% | 2.04% |
| Wax (g/m$^2$) | 0.895 | 0.642 |
| DW content | 6.08% | 5.78% |
| Bulblets per grain of biomass | 1.22 | 1.11 |
| Rate of photosynthesis | 3.01 | 3.72 |
| Leaf area under stomata | 7.88% | 12.51% |

Example 10

Figure 8:
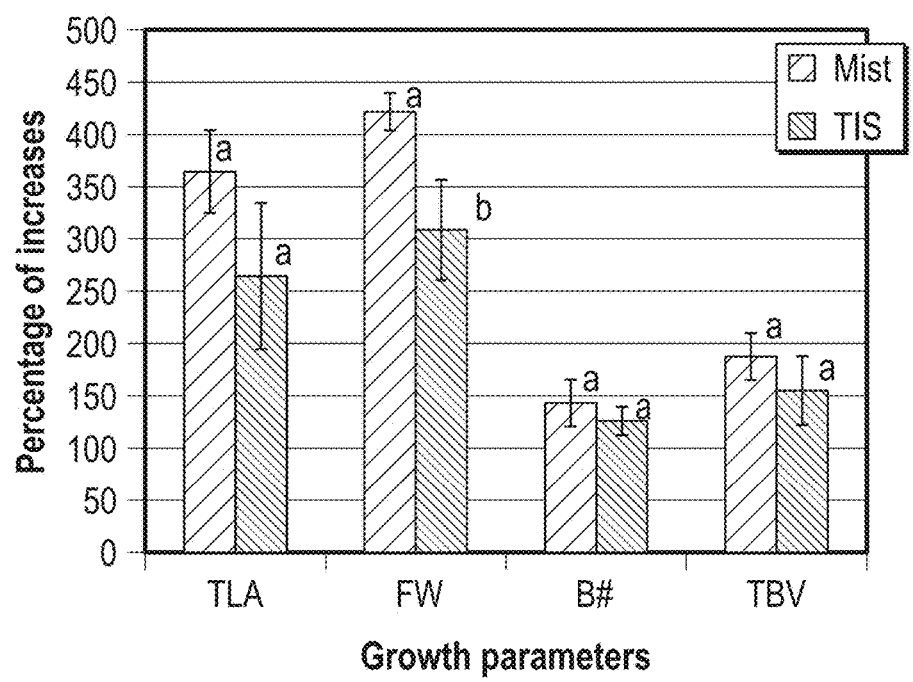
FIG. 8 illustrates the effect of application of medium either by misting (MIST) or by temporary immersion (TIS), upon percent increase in Total Leaf Area (TLA), Fresh Weight (FW), Number of bulbs (B#) and Total Bulb Volume (TBV) after 40 day culture, wherein the different letters above the bars showed significant difference at P<5% and the standard deviation from the mean values is also indicated in accordance with an example of the invention.

To standardize the mode of application of medium for optimal growth of plantlets, medium was applied either in the form of mist or simply filled up in the troughs of the bioreactors, until the plantlets were partially submerged at the bottom. Data on variations in growth parameters was recorded on the 40$^{th}$ day. Significant differences were observed only in percent increase of FW, which was higher in misting than in temporary immersion culture. Apart from this, TLA, B#, TBV though higher in misting, the differences were not significant. Other growth parameters like starch content, dry weight percentage and wax content were higher in plantlets raised through temporary immersion culture, than the ones cultured under misting (Table 3, FIG. 8). Proliferation rate, which is an important deciding factor, was much higher (1.11 bulblets per cluster) for plantlets cultured under misting. The advantages of higher rate of proliferation and increase in FW upon culture of plantlets in mist, added with the convenience in misting (short operation cycle as less medium was required), outweighed the minor drawbacks due to relatively lower starch content, dry weight percentage and wax content, and therefore, culture of *Lilium* plantlets under mist was chosen for further studies.

TABLE 3

Comparison of growth parameters of plantlets raised in bioreactor under misting and temporary immersion (TIS) modes

| | Misting | TIS |
|---|---|---|
| Increase in TLA (Mean) | 365.47% | 265% |
| Increase in FW (Mean) | 418.94% | 307% |
| Increase in TBV (Mean) | 187.42% | 154% |
| Total chlorophyll content (mg/g) | 6.14 | 6.01 |
| Starch in bulbs (%; w/w) | 3.09% | 3.58% |
| Wax (g/m$^2$) | 0.642 | 1.034 |
| DW content | 6.08% | 6.49% |

TABLE 3-continued

Comparison of growth parameters of plantlets raised in bioreactor under misting and temporary immersion (TIS) modes

| | Misting | TIS |
|---|---|---|
| Bulblets per gram of biomass | 1.11 | 0.49 |
| Rate of photosynthesis | 3.72 | 3.77 |
| % of leaf area under stomata | 12.51% | 12.77% |

Example 11

Figure 9:
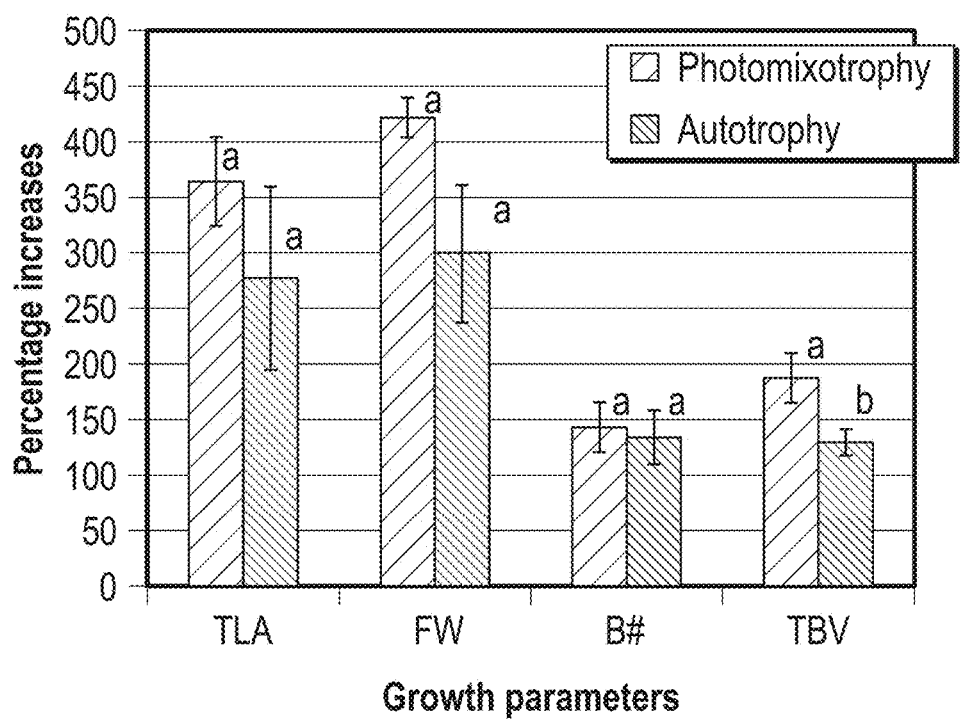
FIG. 9 illustrates the variation in percent increase in TLA, FW, B# and TBV in plantlets raised photomixotrophically or autotrophically after 40 day culture, wherein the different letters above the bars showed significant difference at P<5%, the standard deviation from the mean values are also indicated in accordance with an example of the invention.

Though statistically, the differences in TLA, FW, B# in the plantlets raised photomixotrophically and photoautotrophically were insignificant, these were lower in the cultures raised photoautotrophically (Table 4, FIG. 9). The differences in TBV and their starch content (Table 7) were however, significant. Thus, it was inferred that sucrose was essential especially for accumulation of nutrient reserves in the form of starch.

TABLE 4

Comparison of growth parameters of plantlets raised in bioreactor under photomixotrophic and photoautotrophic conditions

| | Photomixotrophic culture | Photoautotrophic culture |
|---|---|---|
| Increase in TLA (Mean) | 365.47% | 277.12% |
| Increase in FW (Mean) | 418.94% | 297.68% |
| Increase in bulb number (Mean) | 142.71% | 125% |
| Increase in TBV (Mean) | 187.42% | 127.62% |
| Total chlorophyll content (mg/g) | 6.14 | 5.87 |
| Starch in bulbs (%; w/w) | 3.09% | 2.63% |
| Wax (g/m$^2$) | 0.642 | 0.613 |
| DW content | 6.08% | 6.12% |
| Bulblets per gram of biomass | 1.11 | 0.82 |
| Rate of photosynthesis | 3.72 | 3.70 |
| Leaf area under stomata | 12.51% | 12.33% |

Micro propagation is an important means for meeting the growing demands of commercial plants and continuous efforts are being made to bring about improvements in terms of bulking up production and lowering costs. In this regard, use of specially designed apparatus/bioreactor vessel having capacity to handle large volumes of plants and means to finely control the environment, assumes significance. The apparatus is made of autoclavable transparent material equipped with means for application of nutrient medium in the form of mist, in addition to simple filling at the bottom. The apparatus's design facilitated convenient inoculation of a large number of explants. Additionally, an in-line UV disinfection unit was installed which served as a powerful check upon contaminants in the re-circulating nutrient medium. The system also offered advantage of connecting many such apparatus for enhanced efficiency. A large number of growth parameters were tested and results showed that the plants cultured in apparatus fared better than the ones raised in other conventional apparatus.

The apparatus, as disclosed above, is made-up of transparent polycarbonate plastic resin—light weight, strong and corrosion-proof, ensuring better light availability to the plants growing aseptically. The design of the apparatus is essentially suited for accommodation of a large number of explants for prolonged culture. The provision of the support arm structure (linking mechanism 4) for the lid of the apparatus keeps the lid in an elevated position providing ample accessibility to the base trough for performing inoculations, at the same time avoiding any constraint of working space on the laminar flow. The apparatus could be conveniently handled in a standard 6 feet wide laminar flow hood. The explant holding trays, under different configurations could accommodate different types of explants—shoots/callus.

The apparatus, as disclosed above, is configured for application of liquid nutrient medium either by spraying or by simple filling. Also, the complete removal of liquid medium to enable temporary immersion is also possible in the apparatus. The inlets of the apparatus may also be used for bringing about forced ventilation inside the apparatus. Each time during spraying, the plantlets were washed and thus there is no buildup of toxic substances.

The apparatus, as disclosed above, generates plants/seeds, etc. identical in characteristics, because of the uniformity in their growth conditions. The pneumatic pressure assisted mechanism for liquid supply to the bioreactors was capable of transmitting liquid at high flow rates and at high pressures; which is pre-requisite for inducing misting simultaneously in more than one bioreactor (upto five) connected in parallel. For further scale-up, slight modifications are likely to support liquid medium supply to even greater number of bioreactors.

Multiple apparatuses may be simultaneously operated for scale up of the process. The apparatus is further configured for nutrient medium recycling to bring about maximum utilization of the nutrients. The apparatus provides for means for forced ventilation at controlled rates. This was useful in simply bringing about gaseous exchanges during the early stages of culture, and to promote hardening of the plantlets during the later stages so that a separate treatment for hardening could be obliterated.

The apparatus provides for a provision of a side tube in the medium supply tanks allowed for monitoring of loss of water by evaporation, and the same could be made up by addition of sterile distilled water through an additional tank. This helped in avoiding concentration of the nutrient medium thereby, maintaining a constant osmolality.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component of any or all the claims.

While specific language has been used to describe the disclosure, any limitations arising on account of the same are not intended. As would be apparent to a person in the art, various working modifications may be made to the apparatus in order to implement the inventive concept as taught herein.

What claimed is:

1. An apparatus for growing plants or tissues under aseptic conditions, comprising:
    a lid;
    a base compartment; and
    a linking mechanism, connecting the lid and the base compartment; the linking mechanism being provided with a locking mechanism, wherein the linking mechanism is movable from a locked position to an un-locked position and vice-versa, wherein in the locked position, the locking mechanism holds the lid in an abutting closed relation with respect to the base compartment and wherein the linking mechanism is configured so that, when it is in the un-locked position, the linking mechanism automatically lifts the lid to an elevated-suspended position with respect to the base compartment thereby providing an access route to reach the base compartment, wherein the linking mechanism comprises:

at least one first member having a first end and a second end; the first end of the first member being angularly connected to a lateral surface of the base compartment;

at least one second member having a top end and a bottom end; the bottom end of the second member being pivotally connected to the second end of the first member;

at least one third member having a top and bottom end; the bottom end of the third member being pivotally connected to the bottom end of the second member and the top end of the third member connected to a lateral surface of the lid; and at least one fourth member having a top and bottom end; the bottom end of the fourth member being pivotally connected to the top end of the second member and the top end of the fourth member connected to a lateral surface of the lid.

2. The apparatus as claimed in claim 1, wherein the lid comprises:
at least one of:
at least one nutrient medium supply channel; and
at least fogger configured to enable at least one ventilation selected from the group consisting of fogging ventilation, misting ventilation, and forced ventilation within the apparatus.

3. The apparatus as claimed in claim 1, wherein the base compartment comprises a nutrient entry port at an elevated position; a base unit located below the nutrient entry port; wherein the base unit comprises holding trays and a handle attached to the holding trays.

4. The apparatus as claimed in claim 3, wherein the base compartment has a first drain port at an elevation lower than the holding tray.

5. The apparatus as claimed in claim 4, wherein the base-compartment has a second drain port at an elevation higher than the first drain port; the second drain port being at an elevation higher than the holding tray.

6. The apparatus as claimed in claim 3, wherein the base unit has a support structure configured to locate the holding trays at a predetermined position.

7. The apparatus as claimed in claim 3, wherein a floor of the base unit is inclined with respect to a horizontal axis.

8. The apparatus as claimed in claim 1, at least two springs configured to automatically lift the lid upwards, wherein the at least two springs comprise a first spring positioned at a pivotal connection between the second and the third members, and a second spring positioned at a pivotal connection between the second and the fourth members.

9. The apparatus as claimed in claim 1, wherein the apparatus is a bioreactor vessel.

10. The apparatus as claimed in claim 1, wherein the lid further comprises an inverted U-shaped overhang enclosing a curved belt of non-absorbent pad to act as a cushion for disallowing contaminants from entering into the apparatus.

11. The apparatus as claimed in claim 10, wherein the non-absorbent pad is a cotton pad.

12. A system for growing plants or tissues under aseptic conditions, comprising an apparatus and a tank,
the apparatus comprising;
a first lid;
a base compartment; and
a linking mechanism, connecting the first lid and the base compartment; the linking mechanism being provided with a locking mechanism, wherein the linking mechanism is movable from a locked position to an un-locked position and vice-versa, wherein in the locked position, the locking mechanism holds the first lid in an abutting closed relation with respect to the base compartment and wherein the linking mechanism is configured so that, when it is in the un-locked position, the linking mechanism automatically lifts the first lid to an elevated-suspended position with respect to the base compartment thereby providing an access route to reach the base compartment, wherein the linking mechanism comprises:

at least one first member having a first end and a second end; the first end of the first member being angularly connected to a lateral surface of the base compartment;

at least one second member having a top end and a bottom end; the bottom end of the second member being pivotally connected to the second end of the first member;

at least one third member having a top and bottom end; the bottom end of the third member being pivotally connected to the bottom end of the second member and the top end of the third member connected to a lateral surface of the first lid; and at least one fourth member having a top and bottom end; the bottom end of the fourth member being pivotally connected to the top end of the second member and the top end of the fourth member connected to a lateral surface of the first lid;

the tank for providing a nutrient material to the apparatus, comprising:
a body containing the nutrient material;
a second lid provided with a sealing-gasket positioned on top of the body and fastened to the body via a plurality of fastening devices;
a plurality of sealed diaphragm valves positioned on the second lid and configured to provide air compression/release, which are provided for an inlet/outlet for a liquid medium; and
a liquid medium supply port connected to one or more of said valves for supplying the liquid medium to the body.

13. The system as claimed in claim 12, further comprising an outlet connected to the tank and configured to ensure complete draining of the content from inside.

14. An apparatus for growing plants or tissues under aseptic conditions, comprising:
a lid;
a base compartment; and
a linking mechanism, connecting the lid and the base compartment; the linking mechanism being provided with a locking mechanism, wherein the linking mechanism is movable from a locked position to an un-locked position and vice-versa, wherein in the locked position, the locking mechanism holds the lid in an abutting closed relation with respect to the base compartment and wherein the linking mechanism is configured so that, when it is in the un-locked position, the linking mechanism automatically lifts the lid to an elevated-suspended position with respect to the base compartment thereby providing an access-route to reach the base compartment;

wherein the linking mechanism comprises:
- at least one first member having a first end and a second end; the first end of the first member being angularly connected to a lateral surface of the base compartment;
- at least one second member having a top end and a bottom end; the bottom end of the second member being pivotally connected to the second end of the first member;
- at least one third member having a top and bottom end; the bottom end of the third member being pivotally connected to the bottom end of the second member and the top end of the third member connected to a lateral surface of the lid;
- at least one fourth member having a top and bottom end; the bottom end of the fourth member being pivotally connected to the top end of the second member and the top end of the fourth member connected to a lateral surface of the lid; and
- at least two springs configured to automatically lift the lid upwards, wherein the at least two springs comprise a first spring positioned at a pivotal connection between the second and the third members and a second spring positioned at a pivotal-connection between the second and the fourth members.

* * * * *